United States Patent
Muranaka et al.

(10) Patent No.: US 9,556,211 B2
(45) Date of Patent: Jan. 31, 2017

(54) METAL COMPLEX COMPOUND, HYDROGEN PRODUCTION CATALYST AND HYDROGENATION REACTION CATALYST EACH COMPRISING THE METAL COMPLEX COMPOUND, AND HYDROGEN PRODUCTION METHOD AND HYDROGENATION METHOD EACH USING THE CATALYST

(75) Inventors: Makoto Muranaka, Okayama (JP); Toshiyuki Oshiki, Okayama (JP)

(73) Assignee: National University Corporation Okayama University, Okayama-shi (JP)

( * ) Notice: Subject to any disclaimer, the term of this patent is extended or adjusted under 35 U.S.C. 154(b) by 141 days.

(21) Appl. No.: 13/989,229

(22) PCT Filed: Nov. 24, 2011

(86) PCT No.: PCT/JP2011/077061
§ 371 (c)(1),
(2), (4) Date: May 23, 2013

(87) PCT Pub. No.: WO2012/070620
PCT Pub. Date: May 31, 2012

(65) Prior Publication Data
US 2013/0244865 A1 Sep. 19, 2013

(30) Foreign Application Priority Data
Nov. 25, 2010 (JP) .................. 2010-262610

(51) Int. Cl.
| | | |
|---|---|---|
| C01B 3/22 | (2006.01) | |
| B01J 31/20 | (2006.01) | |
| C07F 15/00 | (2006.01) | |
| C07C 5/03 | (2006.01) | |
| C07C 5/09 | (2006.01) | |
| C07F 15/02 | (2006.01) | |
| H01M 8/06 | (2016.01) | |
| B01J 31/24 | (2006.01) | |
| C07F 9/50 | (2006.01) | |

(52) U.S. Cl.
CPC ............ *C07F 15/0033* (2013.01); *B01J 31/20* (2013.01); *B01J 31/2409* (2013.01); *B01J 31/2414* (2013.01); *C01B 3/22* (2013.01); *C07C 5/03* (2013.01); *C07C 5/09* (2013.01); *C07F 9/5045* (2013.01); *C07F 15/004* (2013.01); *C07F 15/008* (2013.01); *C07F 15/0053* (2013.01); *C07F 15/025* (2013.01); *H01M 8/0606* (2013.01); *C01B 2203/0277* (2013.01); *C01B 2203/1064* (2013.01); *C07C 2531/24* (2013.01); *Y02E 60/50* (2013.01)

(58) Field of Classification Search
None
See application file for complete search history.

(56) References Cited

U.S. PATENT DOCUMENTS

| | | |
|---|---|---|
| 3,488,383 A | 1/1970 | Coffey |
| 5,128,296 A | 7/1992 | Matson et al. |
| 7,368,200 B2 | 5/2008 | Zhu et al. |
| 7,939,461 B2 | 5/2011 | Fukuzumi et al. |
| 8,133,464 B2 | 3/2012 | Laurenczy et al. |

FOREIGN PATENT DOCUMENTS

| | | |
|---|---|---|
| JP | 51138614 A | 11/1976 |
| JP | 2003123821 A | 4/2003 |
| JP | 2009078200 A | 4/2009 |
| JP | 2010506818 A | 3/2010 |
| WO | 2007076595 A1 | 7/2007 |
| WO | 2008059630 A1 | 5/2008 |

OTHER PUBLICATIONS

Musco et al. Journal of Organometallic Chemistry, 228(1), C15-C18.*
Sezen et al. JACS, 2005, 127, 5284-5285.*
Buhling et al. Journal of Molecular Catalysis A: Chemical 98, 1995, 69-80.*
Decker et al. J. Chem. Soc., Dalton Trans., 1999, 3507-3513.*
Boddien, Albert et al., "Continuous Hydrogen Generation from Formic Acid: Highly Active and Stable Ruthenium Catalysts", Adv. Synth. Catal. 2009, pp. 2517-2520, vol. 351, Wiley-VCH Verlag GmbH & Co.
Buhling, Armin et al., "Rhodium catalysed hydroformylation of higher alkenes using amphiphilic ligands: part 2", Journal of Molecular Catalysis, 1997, pp. 297-308, vol. 116, Elsevier Science B.V.
Fellay, Celine et al., "A Viable Hydrogen-Storage System Based on Selective Formic Acid Decomposition with a Ruthenium Catalyst", Angew. Chem. Int. Ed., 2008, pp. 3966-3968, vol. 47, Wiley-VCH Verlag GmbH & Co.

(Continued)

*Primary Examiner* — Yun Qian
(74) *Attorney, Agent, or Firm* — The Webb Law Firm

(57) ABSTRACT

Provided is a catalyst for producing hydrogen, which catalyst has higher performance than conventional catalysts since, for example, it exhibits a certain high level of activity in an aqueous formic acid solution at high concentration even without addition of a solvent, amine and/or the like. The metal phosphine complex is a metal phosphine complex represented by General Formula (1): $MH_m(CO)L_n$, wherein M represents an iridium, iron, rhodium or ruthenium atom; in cases where M is an iridium or rhodium atom, m=3 and n=2, and in cases where M is an iron or ruthenium atom, m=2 and n=3; and the number n of Ls each independently represent a tri-substituted phosphine represented by General Formula (2): $PR^1R^2R^3$. The catalyst for producing hydrogen comprises the metal phosphine complex as a constituent component.

1 Claim, 4 Drawing Sheets

(56) References Cited

OTHER PUBLICATIONS

Fukuzumi, Shunichi et al., "Unusually Large Tunneling Effect on Highly Efficient Generation of Hydrogen and Hydrogen Isotopes in pH-Selective Decomposition of Formic Acid Catalyzed by a Heterodinuclear Iridium—Ruthenium Complex in Water", Journal of American Chemical Society, 2010, pp. 1496-1497, vol. 132, American Chemical Society.

Himeda, Yuichiro, "Highly efficient hydrogen evolution by decomposition of formic acid using an iridium catalyst with 4,4'-dihydroxy-2,2'-bipyridine", Green Chemistry, 2009, pp. 2018-2022, vol. 11, The Royal Society of Chemistry.

Huang, Yunjie et al., "Novel PdAu@Au/C Core-Shell Catalyst: Superior Activity and Selectivity in Formic Acid Decomposition for Hydrogen Generation", Chemistry of Materials, 2010, pp. 5122-5128, vol. 22, American Chemical Society.

Krompiec, Stanislaw et al., "Isomerization of allyl aryl ethers to their 1-propenyl derivatives catalysed by ruthenium complexes", Journal of Molecular Catalysis, 2004, pp. 29-40, vol. 219, Elsevier B.V.

Li, Cheng et al., "Synthesis of p-Alkoxylphenyldibenylphosphines and Their Application in Rhodium Catalyzed Hydroformylation of 1—Decene", Journal of Sichuan University, Sep. 2006, pp. 102-106, vol. 38, No. 5, with English Abstract.

Li, Xueli et al, "Hydrogen Generation from Formic Acid Decomposition with a Ruthenium Catalyst Promoted by Functionalized Ionic Liquids", ChemSusChem, 2010, pp. 71-74. vol. 3, Wiley-VCH Verlag GmbH & Co.

Palo, Daniel R. et al., "Effect of Ligand Modification on Rhodium-Catalyzed Homogeneous Hydroformylation in Supercritical Carbon Dioxide", Organometallics, 2000, pp. 81-86, vol. 19, American Chemical Society.

Vol'Pin, M.E. et al., "Reduction of Olefins and Acetylenes by Means of Formic Acid and Formates in Presence of Transition Metals Complexes", Tetrahedron Letters, 1971, pp. 4435-4438, No. 46.

Yasaka, Yoshiro et al., "Kinetic and Equilibrium Study on Formic Acid Decomposition in Relation to the WaterGas-Shift Reaction", J. Phys. Chem. A, 2006, pp. 11082-11090, vol. 110, No. 38, American Chemical Society.

Baricelli P J et al: Synthesis, characterization and aqueous-biphase hydrogenation of olefins by the ruthenium complexes Ru(C0)3(TPPMS)2 and RuH2(C0)(TPPMS)3H, Applied Catalysis A: General, ElsevierScience, Amsterdam, NL, vol. 239, No. 1-2, Jan. 30, 2003 (Jan. 30, 2003), pp. 25-34.

Baricelli P J et al: "Synthesis and characterization of Ru(H)2 (CO)(TPPMS)3 and catalytic properties in the aqueous-biphasic hydroformylation of olefins",Applied Catalysis A: General, Elsevier Science, Amsterdam, NL, vol. 263, No. 2, Jun. 10, 2004 (Jun. 10, 2004), pp. 187-191.

Paul J. Roman et al: "Synthesis, bProperties, and Reactions of Monosulfonated Triphenylphosphine (PPh 2 (m-C 6 H 4 SO 3 K) = TPPMS) Complexes of Iridium (I). Crystal and Molecular Structure of [N(Ch 2 C 6 H 5)(C 2 H 5) 3 + ] [PPh 2 ( m-C 6 H 4 So 3 ) - ].H 2 0",Organometallics, vol. 16, No. 7, Apr. 1, 1997 (Apr. 1, 1997), pp. 1484-1490.

Database CA [Online] Chemical Abstracts Service, Columbus, Ohio, US; Sezen, Bengue et al: "Selective and Catalytic Arylation of N-Phenylpyrrolidine: sp3 C—H Bond Functionalization in the Absence of a Directing Group", XP002721116, & Sezen, Bengue et al: "Selective and Catalytic Arylation of N-Phenylpyrrolidine: sp3 C—H Bond Functionalization in the Absence of a Directing Group", Journal of the American Chemical Society, 127(15), 5284-5285 Coden.

Database CA [Online] Chemical Abstracts Service, Columbus, Ohio, US; Angoletta, Maria et al: "Hydridobis(acetato)bis(triarylphosphine)iridium(III) complexes", XP002721117, retrieved from STN Database accession No. 1983:190611 & Angoletta, Maria et al: "Hydridobis (acetato)bis (triarylphosphine)iridium(III) complexes", Gazzetta Chimica Italiana , 112(11-12),549-51 Coden: GCITA9; ISSN: 0016-5603, 1982.

Christian Belger et al: "A Selective Ru-Catalyzed Semi reduction of Alkynes to Z Olefins under Transfer-Hydrogenation Conditions", Chemistry—A European Journal, vol. 16, No. 40, Oct. 25, 2010 (Oct. 25, 2010), pp. 12214-12220.

Ligthart G B W L et al: "Highly sustainable catalytic dehydrogenation of alcohols with evolution of hydrogen gas", Tetrahedron Letters, Pergamon, GB, vol. 44, No. 7, Feb. 10, 2003 (Feb. 10, 2003), pp. 1507-1509.

* cited by examiner

METAL COMPLEX COMPOUND, HYDROGEN PRODUCTION CATALYST AND HYDROGENATION REACTION CATALYST EACH COMPRISING THE METAL COMPLEX COMPOUND, AND HYDROGEN PRODUCTION METHOD AND HYDROGENATION METHOD EACH USING THE CATALYST

TECHNICAL FIELD

The present invention relates to a method for producing hydrogen from formic acid using a metal complex catalyst, and the like. More specifically, the present invention relates to: a novel metal complex compound having a specific chemical structure; a catalyst for producing hydrogen by decomposition reaction of formic acid and a catalyst for hydrogenation reactions, which catalysts comprise the metal complex compound; and a process of producing hydrogen and a method of hydrogenation using the catalysts.

BACKGROUND ART

In recent years, formic acid, similarly to methanol and organic hydrides, is being studied all over the world as a promising hydrogen-storing material, because of its ability to produce hydrogen at room temperature. Formic acid fuel cells (for example, see Patent Document 1) have already been begun to be supplied to the market.

For production of hydrogen from formic acid in production of fuel cells and the like, there is a method using a microorganism that generates hydrogen using formic acid as the energy source (biocatalyst) (Patent Document 2). However, methods using chemical catalysts, which are excellent in heat resistance, acid resistance and the like compared to biocatalysts, are being extensively developed at home and abroad. Representative examples of the methods using chemical catalysts include the high-temperature pyrolysis method (Non-patent Document 1), solid catalyst method (Non-patent Document 2) and metal complex catalyst method (Patent Documents 3 to 5, Non-patent Documents 3 to 7).

On the other hand, as iridium hydride complexes represented by the general formula $IrH_3(CO)L_2$, compounds having $PPh_3$, $PCy_3$, $PEt_3$, $PPh_2(4\text{-MePh})$ and/or $PEt_2Ph$ [wherein Ph is an abbreviation for a phenyl group, Cy is an abbreviation for a cyclohexyl group, Et is an abbreviation for an ethyl group, and Me is an abbreviation for a methyl group; the same applies hereinafter] as a ligand Ls are known (according to search with Scifinder). Further, as iridium complexes represented by the general formula $Ir(acac)L_2$ [wherein acac is an abbreviation for acetylacetonato; the same applies hereinafter], compounds having $PPh_3$, $PMePh_2$, $PMe_3$ and/or $PPh_2Py$ [wherein Py is an abbreviation of a pyridyl group; the same applies hereinafter] as a ligand L(s) are known, and, as iridium hydride complexes represented by the general formula $IrH_3L_3$, compounds having $PPh_3$, $PMe_2Ph$, $PPh(4\text{-MePh})$ and/or $PMePh_2$ as a ligand Ls are known.

For example, in relation to such compounds, Patent Document 6 describes a method wherein, by contacting $IrH_xHal_{3-x}P_{n2}$ or $IrH_xHal_{3-x}(CO)P_{n2}$ (wherein x represents 0 to 3, Pn represents tertiary phosphine or arsine, and Hal represents Cl, Br or I) with a mixture of formic acid and another fatty acid or fatty acid ester, formic acid in the mixture is selectively decomposed. The general description in its specification describes that the above complex is preferably $IrH_3P(PAr_3)_3$ (wherein Ar represents a phenyl group or a substituted phenyl group) (see lines 59-60 in column 1, and claim 5), and $IrH_3(PPh_3)_3$ is used in Examples (see Examples 5, 6, 8 and 9).

However, Patent Document 6 only describes that formic acid at a low concentration can be decomposed in a mixture in which a fatty acid or fatty acid ester coexists (which can also be said to be a formic acid solution containing a fatty acid or fatty acid ester as a solvent). The specification describes that the concentration of formic acid in the above mixture is, for example, 1 to 50% (see the 3rd line from the bottom to the final line in column 1, and claim 7), but the concentration was about 3 to 10% in Examples wherein $IrH_3(PPh_3)_3$ was used (see Examples 5, 6, 8 and 9). Moreover, neither Example in which a complex having a "substituted phenyl group" was used as a complex represented by $IrH_3P(PAr_3)_3$ nor Example in which a complex represented by $IrH_3(CO)P_{n2}$ was used is disclosed at all.

Further, Patent Document 7 describes a method for producing a formic acid or formic acid ester, wherein, in the presence of a catalyst containing a hydride complex of a group VIII transition metal and an aliphatic tertiary amine, a compound represented by the general formula ROH (wherein R represents hydrogen or a hydrocarbon group) (that is, water or an alcohol) is reacted with carbon dioxide and hydrogen. It is described that specific examples of the hydride complex of a group VII transition metal include $(PPh_3)_4RuH_2$, $(PPh_3)_4IrH_3$ and $(PPh_3)_3(CO)RhH$ (see the upper right column in page 2). Further, in Examples, modes wherein a predetermined hydride complex is fed together with methanol, ethanol or water, and carbon dioxide and hydrogen are injected, to produce methyl formate, ethyl formate or formic acid, respectively, are described.

However, although the method described in Patent Document 7 is a method wherein the predetermined complex is used with hydrogen and the like fed separately to produce formic acid or the like (in this process, "hydrogenation of carbon dioxide" occurs), there is neither description nor suggestion on a method wherein hydrogen is obtained from another compound using the above complex and the obtained hydrogen is used to hydrogenate an unsaturated compound (compound having a carbon-carbon unsaturated bond and/or the like). Moreover, Patent Document 7 does not specifically disclose the hydride complex of a group VII transition metal other than those using triphenylphosphine as a ligand. That is, those using phosphine having a substituent other than a phenyl group as a ligand is not specifically disclosed. Moreover, in the hydrogenation reaction described in Patent Document 7, combined use of an aliphatic tertiary amine is described as an essential requirement.

Non-patent Document 8 describes a method wherein formic acid (and, preferably, a formic acid salt) is used in the presence of a transition metal complex to hydrogenate (reduce) olefin and acetylene. It is described that specific examples of the transition metal complex used for hydrogenation of olefin (1-octene) include $(Ph_3P)_2Ir(CO)Br$, $(Ph_3P)_3Ir(CO)H$, $(Ph_3P)_2IrH_2Cl$ and $(Ph_3P)_2Ir(CO)_2H$ (Table I).

However, Non-patent Document 8 does not specifically disclose a transition metal (e.g., iridium) complex represented by the general formula $MH_m(CO)L_n$ other than those using triphenylphosphine as a ligand. That is, those using phosphine having a substituent other than a phenyl group as a ligand is not specifically disclosed. Moreover, for unsaturated compounds having a carbon-carbon triple bond such as 3-hexyne and phenylacetylene, the document does not specifically disclose a mode other than one using $(Ph_3P)_3RhCl$ as a transition metal complex. Further, in cases where the reaction is carried out at a temperature of about 60° C., especially in cases where only formic acid is used and no formic acid salt is used in combination, the yield of the hydrogenated product tends to be low.

CITATION LIST

Patent Documents

[Patent Document 1] WO2007/076595
[Patent Document 2] JP 2003-123821 A
[Patent Document 3] WO2008/059630
[Patent Document 4] JP 2009-78200 A
[Patent Document 5] JP 2010-506818 A
[Patent Document 6] U.S. Pat. No. 3,488,383 B
[Patent Document 7] JP S51-138614 A Non-Patent Documents

[Non-patent Document 1] M. Nakahara, J. Phys. Chem. A, 2006, 110, 11082
[Non-patent Document 2] W. Xing, Chem. Mater., 2010, 22, 5122
[Non-patent Document 3] M. Beller, Adv. Synth. Catal., 2009, 351, 2517
[Non-patent Document 4] S. Fukuzumi, J. Am. Chem. Soc., 2010, 132, 1496
[Non-patent Document 5] G. Laurenczy, Angew. Chem. Int. Ed., 2008, 47, 3966
[Non-patent Document 6] Y. Deng, Chem Sus Chem, 2010, 3, 71
[Non-patent Document 7] Y. Himeda, Green Chem., 2009, 11, 2018
[Non-patent Document 8] M. E. Vol'pin et al., Tetrahedron Letters, 1971, 46, 4435-4438

In the high-temperature pyrolysis method, decarboxylation of formic acid ($HCOOH \rightarrow CO+H_2O$) occurs to generate carbon monoxide as a by-product gas, and a high temperature condition (not less than 200° C.) is required. Further, the catalyst used in the solid catalyst method (PdAu@Au/C core shell-type catalyst) has low activity in spite of the fact that large amounts of platinum and palladium, which are expensive noble metals, are used.

On the other hand, the catalyst used in the conventional metal complex method has low activity in a formic acid solution at a high concentration (not less than 50 vol %, under strongly acidic conditions), and a solvent other than water, and formic acid salt, amine and the like need to be added (however, use of a formic acid solution at a low concentration results in a low hydrogen storage density).

An object of the present invention is to provide a catalyst for production of hydrogen, which has higher performance than conventional catalysts in view of, for example, that a certain high activity can be obtained in an aqueous formic acid solution at a high concentration even without addition of a solvent other than water, or amine or the like.

SUMMARY OF THE INVENTION

The present inventors discovered: that the above problems can be solved with metal complexes such as iridium having phosphine as a ligand since they can be excellent catalysts for production of hydrogen by dehydrogenation of formic acid; that metal complexes having as a ligand phosphine having a certain functional group (for example, a substituted aryl group) have remarkable catalytic activity; and that such catalysts can be used to perform hydrogenation reaction of unsaturated compounds; thereby completing the present invention.

That is, the present invention includes the following contents.

[1] A metal phosphine complex represented by General Formula (1)

$$MH_m(CO)L_n \qquad (1)$$

[wherein in Formula (1),

M represents an iridium, iron, rhodium or ruthenium atom;

in cases where M is an iridium or rhodium atom, m=3 and n=2, and in cases where M is an iron or ruthenium atom, m=2 and n=3;

the number n of Ls each independently represent a tri-substituted phosphine represented by General Formula (2)

$$PR^1R^2R^3 \qquad (2)$$

(wherein in Formula (2), $R^1$, $R^2$ and $R^3$ each independently represent an optionally substituted aromatic hydrocarbon group having from 6 to 15 carbons or an optionally substituted alicyclic hydrocarbon group having from 5 to 10 carbons)

wherein the cases where all Ls are tri-substituted phosphines wherein all of $R^1$, $R^2$ and $R^3$ are an unsubstituted phenyl group(s), a phenyl group(s) substituted by a straight hydrocarbon group(s), a sulfo group(s) or by a halogen(s), or an unsubstituted cyclohexyl group(s) are excluded].

[2] The metal phosphine complex according to the item 1, wherein the tri-substituted phosphine represented by the General Formula (2) comprises at least one optionally substituted cyclohexyl group or 4-dialkylaminophenyl group.

[3] The metal phosphine complex according to the item 1 or 2, wherein the tri-substituted phosphine represented by the General Formula (2) is at least one selected from the group consisting of tri(4-dialkylaminophenyl)phosphine, di(4-dialkylaminophenyl)phenylphosphine, 4-dialkylaminophenyldiphenylphosphine, trimethylcyclohexylphosphine, methylcyclohexyldicyclohexylphosphine, dicyclohexyl(4-dialkylaminophenyl)phosphine and cyclohexyldi(4-dialkylaminophenyl)phosphine.

[4] A catalyst for producing hydrogen by the formic acid decomposition reaction ($HCOOH \rightarrow H_2+CO_2$), the catalyst comprising as a constituent component the metal phosphine complex according to any one of the items 1 to 3.

[5] The catalyst for producing hydrogen according to the item 4, further comprising as a constituent component an amine or a phosphine.

[6] The catalyst for producing hydrogen according to the item 5, wherein the amine is at least one amine selected from the group consisting of an aliphatic amine, an alicyclic amine, an aromatic amine and a heterocyclic amine.

[7] The catalyst for producing hydrogen according to the item 6, wherein the phosphine is at least one phosphine selected from the group consisting of a trialiphatic phosphine, a trialicyclic phosphine, a triaromatic phosphine and a triaralkyl phosphine.

[8] A process of producing hydrogen, the process comprising contacting the catalyst for producing hydrogen according to any one of the items 4 to 7 with an aqueous formic acid solution.

[9] The process of producing hydrogen according to the item 8, wherein the contact is performed at a temperature of 0 to 100° C.

[10] The process of producing hydrogen according to the item 8 or 9, wherein the contact is performed in an aqueous formic acid solution having a formic acid concentration of not less than 1% by volume and less than 100% by volume.

[11] The process of producing hydrogen according to any one of the items 8 to 10, wherein the contact is performed in an aqueous formic acid solution having a concentration of the metal phosphine complex of 0.01 to 500 µmol/mL.

[12] A catalyst for hydrogenation reactions, the catalyst comprising as a constituent component the metal phosphine complex according to any one of the items 1 to 3.

[13] The catalyst for hydrogenation reactions according to the item 12, further comprising as a constituent component an amine or a phosphine.

[14] The catalyst for hydrogenation reactions according to the item 13, wherein the amine is at least one amine selected from the group consisting of an aliphatic amine, an alicyclic amine, an aromatic amine and a heterocyclic amine.

[15] The catalyst for hydrogenation reactions according to the item 13, wherein the phosphine is at least one phosphine selected from the group consisting of a trialiphatic phosphine, a trialicyclic phosphine, a triaromatic phosphine and a triaralkyl phosphine.

[16] A method of hydrogenation comprising reacting an unsaturated compound with hydrogen in the presence of the catalyst for hydrogenation reactions according to any one of the items 12 to 15 and an aqueous formic acid solution.

[17] The method of hydrogenation according to the item 16, wherein the unsaturated compound comprises a carbon-carbon double bond and/or a carbon-carbon triple bond.

[18] The method of hydrogenation according to the item 16 or 17, wherein the reaction solution in the hydrogenation reaction has a concentration of the metal phosphine complex of 0.01 to 500 µmol/mL.

[19] A fuel cell comprising as a constituent component the catalyst for producing hydrogen according to any one of the items 4 to 7.

In the present invention, the number of carbon atoms in the aromatic hydrocarbon group, aralkyl group, alicyclic hydrocarbon group or branched hydrocarbon group does not include the number of carbon atoms in the substituent (s) having a carbon atom(s) which may be contained in these functional groups.

The term "optionally substituted" includes both the case where the subject has a substituent(s) and the case where the subject does not have a substituent. The term "each independently" means any of the case where all subjects are the same, the case where all subjects are different from each other, and the case where some of the subjects are the same but some of the subjects are different.

In the following descriptions related to the present invention, the metal phosphine complexes represented by General Formulae (1), (4), (5) and (1') may be abbreviated as the complexes (1), (4), (5) and (1'), respectively. The complexes (1), (4) and (1') may be abbreviated as "(the metal M, for example, iridium) hydride complex", and the complex (5) may be abbreviated as "(the metal M, for example, iridium) complex". Each tri-substituted phosphine represented by General Formula (2) may be abbreviated as the phosphine (2). The metal bidentate ligand complex represented by General Formula (3) may be abbreviated as the complex (3).

Since the catalyst for producing hydrogen provided by the present invention shows high activity in the presence of formic acid in a high concentration range without use of additives, the hydrogen storage density can be remarkably increased using an aqueous formic acid solution at a high concentration; hydrogen can be produced even in a high concentration range at room temperature (25° C.); and the amount of hydrogen produced can be controlled by changing the reaction temperature. Moreover, in cases were such a catalyst for producing hydrogen is used, carbon oxide is not generated, so that utilization of hydrogen does not require a complicated operation for gas separation. Further, the complex used for such a catalyst for producing hydrogen is relatively stable in the air and hence can be easily handled, and the method for synthesizing the complex is simple and hence the cost for producing it is low.

DETAILED DESCRIPTION OF THE INVENTION

Figure 1:
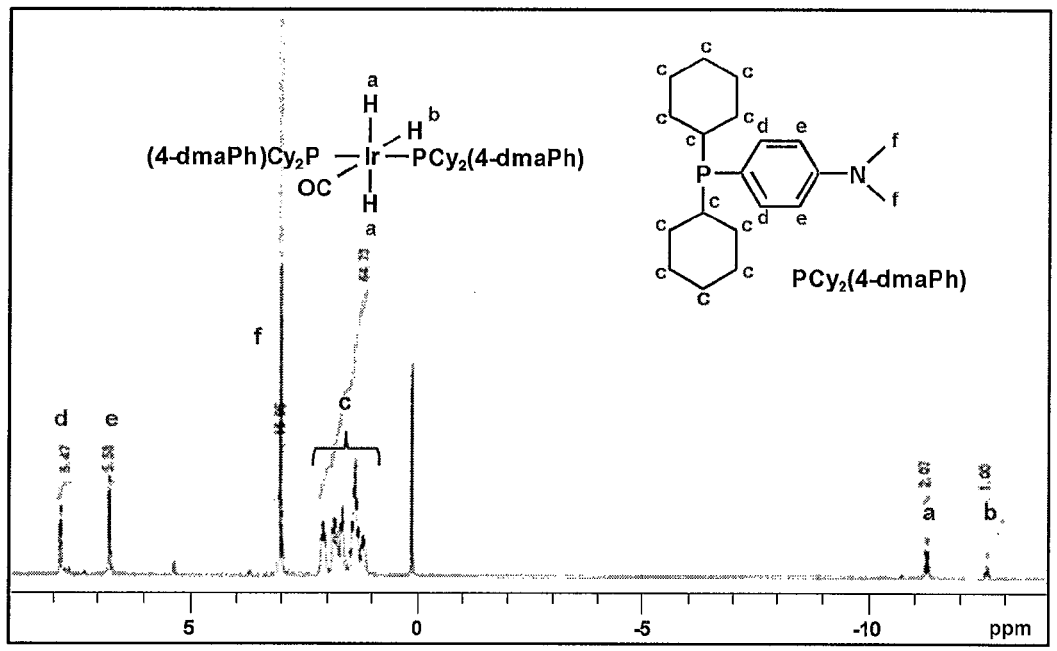
FIG. 1 shows the $^{1}H$ NMR spectrum of the iridium hydride A.
Figure 2:
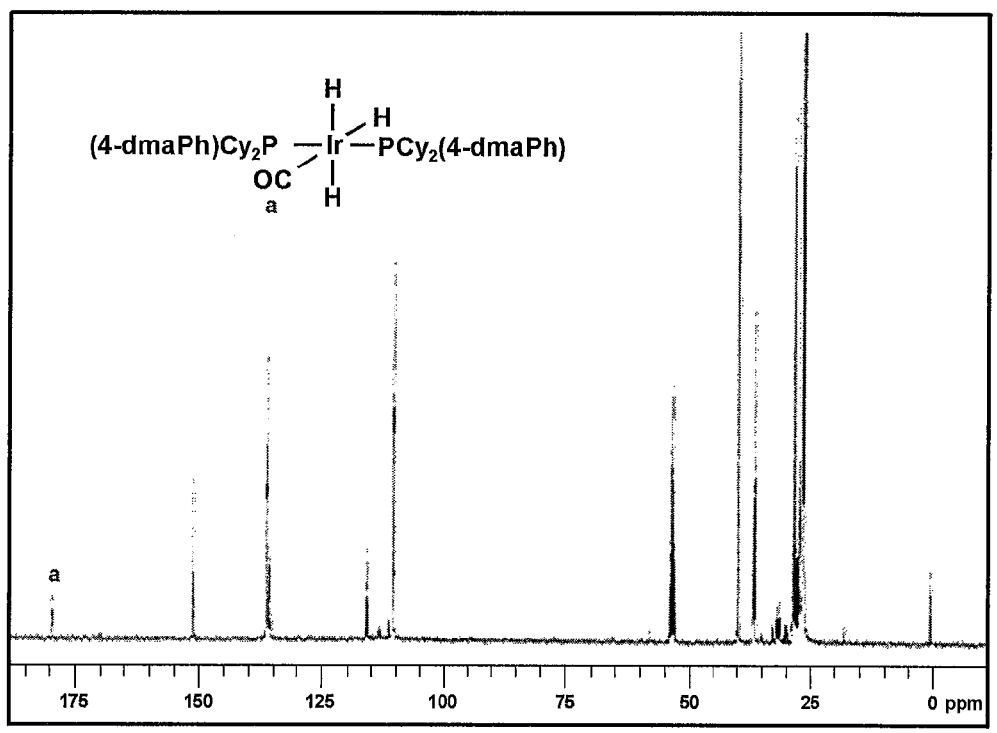
FIG. 2 shows the $^{13}C$ NMR spectrum of the iridium hydride A.
Figure 3:
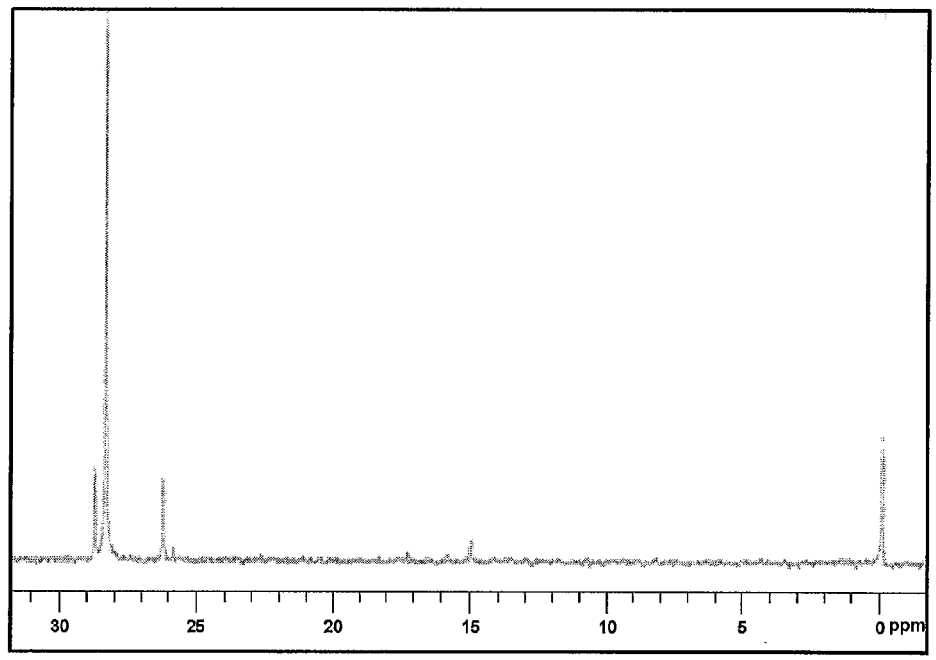
FIG. 3 shows the $^{31}P$ NMR spectrum of the iridium hydride A.
Figure 4:
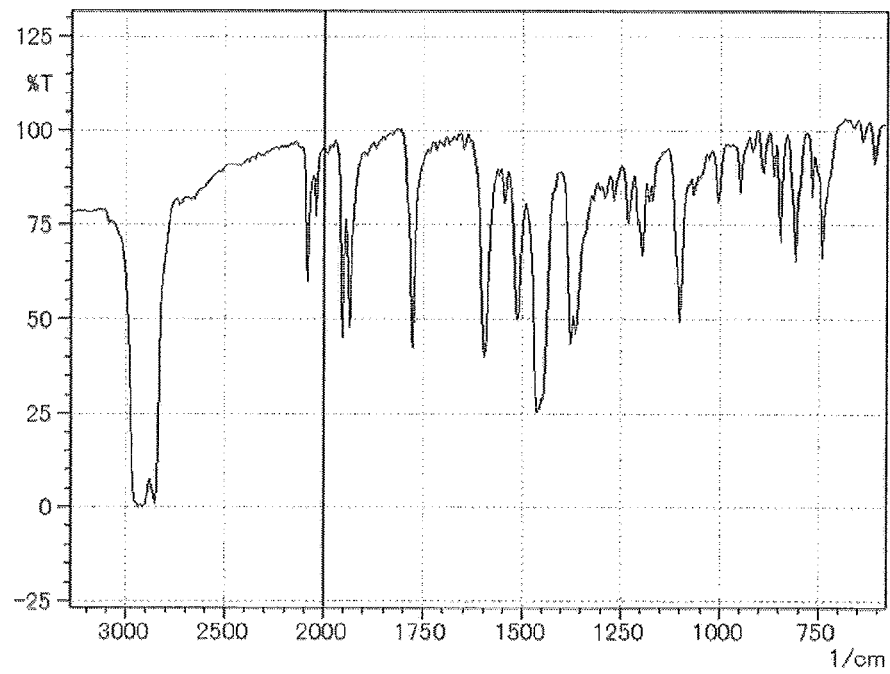
FIG. 4 shows the FT-IR spectrum of the iridium hydride A.

<Metal Phosphine Complex>
The novel metal phosphine complex (Complex (1)) in the present invention is represented by General Formula (1):

$$MH_m(CO)L_n \quad (1)$$

wherein in Formula (1),
M represents an iridium, iron, rhodium or ruthenium atom;
in cases where M is an iridium or rhodium atom, m=3 and n=2, and in cases where M is an iron or ruthenium atom, m=2 and n=3;
the number n of Ls each independently represent a tri-substituted phosphine represented by General Formula (2) (i.e. phosphine (2)):

$$PR^1R^2R^3 \quad (2)$$

wherein in Formula (2), $R^1$, $R^2$ and $R^3$ each independently represent an optionally substituted aromatic hydrocarbon group having from 6 to 15 carbons or an optionally substituted alicyclic hydrocarbon group having from 5 to 15 carbons, wherein the cases where all of $R^1$, $R^2$ and $R^3$ are an unsubstituted phenyl group(s), a phenyl group(s) substituted by a straight hydrocarbon group(s), a sulfo group(s) or by a halogen(s), or an unsubstituted cyclohexyl group(s) are excluded. (That is, a complex is included in the definition according to the Formula (1) even in cases where the complex has a tri-substituted phosphine wherein one or two of $R^1$, $R^2$ and $R^3$ is/are an unsubstituted phenyl group(s), a phenyl group(s) substituted by a straight hydrocarbon group(s), a sulfo group(s) or by a halogen(s), or an unsubstituted cyclohexyl group(s), as long as the remaining substituent(s) is/are a substituent(s) other than an unsubstituted phenyl group(s), a phenyl group(s) substituted by a straight hydrocarbon group(s), a sulfo group(s) or by a halogen(s), or an unsubstituted cyclohexyl group(s).

In other words, the complex (1) includes metal phosphine complexes represented by the General Formulae (11) to (14) below. In the General Formulae (11) to (14), the definition of each of $L^1$, $L^2$ and $L^3$ is the same as that of L in Formula (1).

$$IrH_3(CO)L^1L^2 \tag{11}$$

$$RhH_3(CO)L^1L^2 \tag{12}$$

$$FeH_2(CO)L^1L^2L^3 \tag{13}$$

$$RuH_2(CO)L^1L^2L^3 \tag{14}$$

Examples of the aromatic hydrocarbon group having from 6 to 15 carbons include a phenyl group, naphthyl group and biphenyl group.

Examples of the alicyclic hydrocarbon group having from 5 to 10 carbons include a cyclopentyl group, cyclohexyl group, cyclooctyl group, cyclodecyl group, cyclododecyl group and adamantyl group.

Examples of the substituents of $R^1$, $R^2$ and $R^3$ (that is, the substituents contained in the aromatic hydrocarbon group, alicyclic hydrocarbon group or the like) include halogens (e.g., fluorine), a nitro group, a sulfo group, a hydroxyl group, optionally substituted amino groups having not more than 12 carbon atoms (e.g., a dimethylamino group), hydrocarbon groups having 1 to 6 carbon atoms (e.g., a methyl group), and alkoxy groups having 1 to 6 carbon atoms (e.g., a methoxy group). Each of the substituents described above (for example, the sulfo group) may be forming a salt (for example, the sodium salt). In particular, a tri-substituted phosphine having, as at least one of the $R^1$, $R^2$ and $R^3$, an aromatic hydrocarbon group (s), alicyclichydrocarbon group(s) and/or the like having an optionally substituted amino group having not more than 12 carbon atoms, for example, dimethylamino group, is preferred since it tends to have excellent catalyst performance.

Further, the tri-substituted phosphine represented by General Formula (2) preferably has at least one optionally substituted cyclohexyl group or 4-dialkylaminophenyl group.

Specific examples of such phosphine (2) having an aromatic hydrocarbon group(s) include tri(4-dialkylaminophenyl)phosphine, di(4-dialkylaminophenyl)phenylphosphine and 4-dialkylaminophenyldiphenylphosphine.

Further, specific examples of such phosphine (2) having an alicyclic hydrocarbon group include trimethylcyclohexylphosphine, methylcyclohexyldicyclohexylphosphine, dicyclohexyl(4-dialkylaminophenyl)phosphine and cyclohexyldi(4-dialkylaminophenyl)phosphine.

The following are specific examples of the complex (1) which is a complex represented by $MH_m(CO)L_n$, wherein M represents iridium, and the tri-substituted phosphine $PR^1R^2R^3$ as the ligand L has the substituents $R^1$, $R^2$ and $R^3$ all of which are an optionally substituted aromatic hydrocarbon group(s) having from 6 to 15 carbons and/or an optionally substituted alicyclic hydrocarbon group(s) having from 5 to 10 carbons: trihydride carbonylbis(dicyclohexyl(4-(N,N-dimethylamino)phenyl)phosphine)iridium, trihydride carbonylbis(diphenyl(4-(N,N-dimethylamino)phenyl)phosphine)iridium, trihydride carbonylbis(tricyclopentylphosphine)iridium, trihydride carbonylbis(tricycloheptylphosphine)iridium, trihydride carbonylbis(tricyclooctylphosphine)iridium, trihydride carbonylbis(diphenyl(2-methoxyphenyl)phosphine)iridium, trihydride carbonylbis(4-diphenylphosphanyl benzoic acid, 2-(trimethylsilyl)ethyl ester)iridium, trihydride carbonylbis(2-(diphenylphosphino)benzaldehyde)iridium, trihydride carbonylbis(2-(diphenylphosphino)benzoic acid)iridium, trihydride carbonylbis(4-(diphenylphosphino)benzoic acid)iridium, trihydride carbonylbis((4-hydroxyphenyl)diphenylphosphine)iridium, trihydride carbonylbis(tris(2,6-dimethoxyphenyl)phosphine)iridium, trihydride carbonylbis(tris(4-methoxyphenyl)phosphine)iridium, trihydride carbonylbis(tris(2,4,6-dimethoxyphenyl)phosphine)iridium, trihydride carbonylbis((2-biphenyl)dicyclohexylphosphine)iridium, trihydride carbonylbis(2-dicyclohexylphosphino-2'6'-diisopropylbiphenyl)iridium, trihydride carbonylbis(2-dicyclohexylphosphino-2'6'-dimethoxybiphenyl)iridium, trihydride carbonylbis(2-dicyclohexylphosphino-2'-(N,N-dimethylamino) biphenyl)iridium, trihydride carbonylbis(2-dicyclohexylphosphino-2'4'6'-triisopropylbiphenyl)iridium, trihydride carbonylbis(2-diphenylphosphino-2'-(N,N-dimethylamino)biphenyl)iridium and trihydride carbonylbis(2'-dicyclohexylphosphino-2,6-dimethoxy-1,1'-biphenyl-3-sulfonate sodium hydrate)iridium.

The following are specific examples of the complex (1) which is a complex represented by $MH_m(CO)L_n$, wherein M represents rhodium, and the tri-substituted phosphine $PR^1R^2R^3$ as the ligand L has the substituents $R^1$, $R^2$ and $R^3$ all of which are an optionally substituted aromatic hydrocarbon group(s) having from 6 to 15 carbons and/or an optionally substituted alicyclic hydrocarbon group(s) having from 5 to 10 carbons: trihydride carbonylbis(dicyclohexyl(4-(N,N-dimethylamino)phenyl)phosphine)rhodium, trihydride carbonylbis(tris(4-methoxyphenyl)phosphine)rhodium, trihydride carbonylbis(2-dicyclohexylphosphino-2'-(N,N-dimethylamino)biphenyl)rhodium, trihydride carbonylbis(tricyclooctylphosphine)rhodium and trihydride carbonylbis((4-(N,N-dimethylamino)phenyl)diphenylphosphine)rhodium.

The following are specific examples of the complex (1) which is a complex represented by $MH_m(CO)L_n$, wherein M represents iron, and the tri-substituted phosphine $PR^1R^2R^3$ as the ligand L has the substituents $R^1$, $R^2$ and $R^3$ all of which are an optionally substituted aromatic hydrocarbon group(s) having from 6 to 15 carbons and/or an optionally substituted alicyclic hydrocarbon group(s) having from 5 to 10 carbons: dihydride carbonyl tris(tris(4-methoxyphenyl)phosphine)iron, dihydride carbonyl tris(2-dicyclohexylphosphino-2'-(N,N-dimethylamino)biphenyl)iron, dihydride carbonyl tris(tricyclooctylphosphine)iron and dihydride carbonyl tris((4-(N,N-dimethylamino)phenyl)diphenylphosphine)iron.

The following are specific examples of the complex (1) which is a complex represented by $MH_m(CO)L_n$, wherein M represents ruthenium, and the tri-substituted phosphine $PR^1R^2R^3$ as the ligand L has the substituents $R^1$, $R^2$ and $R^3$ all of which are an optionally substituted aromatic hydrocarbon group(s) having from 6 to 15 carbons and/or an optionally substituted alicyclic hydrocarbon group(s) having from 5 to 10 carbons: dihydride carbonyl tris(dicyclohexyl(4-(N,N-dimethylamino)phenyl)phosphine)ruthenium, dihydride carbonyl tris(tris(4-methoxyphenyl)phosphine)ruthenium, dihydride carbonyl tris(2-dicyclohexylphosphino-2'-(N,N-dimethylamino)biphenyl)ruthenium, dihydride carbonyl tris(tricyclooctylphosphine)ruthenium and dihydride carbonyl tris((4-(N,N-dimethylamino)phenyl)diphenylphosphine)ruthenium.

Another aspect of the present invention provides a method using, as a component of the catalyst for producing hydrogen, a complex having a chemical structure similar to the Formula (1) but having $R^1$, $R^2$ and $R^3$ in the tri-substituted phosphine of Formula (2) as L each of which is not an aromatic hydrocarbon group or alicyclic hydrocarbon group meeting the above definition.

Examples of such a complex include a complex having a tri-substituted phosphine wherein $R^1$, $R^2$ and $R^3$ in Formula (2) as L in Formula (1) each independently represent an optionally substituted aralkyl group having from 7 to 15 carbons or an optionally substituted branched hydrocarbon group having from 3 to 6 carbons. (In the present description, such a metal phosphine complex may be referred to as the complex (1'), and such a tri-substituted phosphine may be referred to as the phosphine (2').)

Examples of the aralkyl group having from 7 to 15 carbons include a benzyl group, phenylethyl group and naphthylmethyl group. These aralkyl groups may have substituents which are the same as those exemplified for the aromatic hydrocarbon group or alicyclic hydrocarbon group. Specific examples of tri-substituted phosphines having such an aralkyl group(s) include tribenzylphosphine and trimethylbenzylphosphine.

Examples of the branched hydrocarbon group having from 3 to 6 carbons include an isopropyl group, sec-butyl group, tert-butyl group, isobutyl group, 2-pentyl group, 3-pentyl group, 2-methyl-2-butyl group, 2-hexyl group, 3-hexyl group and 2-methyl-2-pentyl group. These branched hydrocarbon groups may have substituents which are the same as those exemplified for the aromatic hydrocarbon group or alicyclic hydrocarbon group. Specific examples of tri-substituted phosphines having such an branched hydrocarbon group(s) include triisopropylphosphine, tri-sec-butylphosphine, tri-tert-butylphosphine, triisobutylphosphine, tri-2-pentylphosphine, tri-3-pentylphosphine, tri-2-methyl-2-butylphosphine, tri-2-hexylphosphine, tri-3-hexylphosphine and tri-2-methyl-2-pentylphosphine.

The following are specific examples of the complex (1') which is a complex represented by $MH_m(CO)L_n$, wherein M represents iridium, and the tri-substituted phosphine $PR^1R^2R^3$ as the ligand L has the substituents $R^1$, $R^2$ and $R^3$ at least one of which is neither an optionally substituted aromatic hydrocarbon group having from 6 to 15 carbons nor an optionally substituted alicyclic hydrocarbon group having from 5 to 10 carbons: trihydride carbonylbis(benzyldiphenylphosphine)iridium, trihydride carbonylbis(tert-butyldicyclohexylphosphine)iridium, trihydride carbonylbis(tert-butyldiisopropylphosphine) iridium, trihydride carbonylbis(tert-butyldiphenylphosphine)iridium, trihydride carbonylbis(di-tert-butylneopentylphosphine)iridium, trihydride carbonylbis(di-tert-butylphenylphosphine)iridium, trihydride carbonylbis(isopropyldiphenylphosphine)iridium, trihydride carbonylbis(tribenzylphosphine)iridium, trihydride carbonylbis(tri-tert-butylphosphine) iridium, trihydride carbonylbis(triisobutylphosphine)iridium, trihydride carbonylbis(triisopropylphosphine)iridium, trihydride carbonylbis((4-(N,N-dimethylamino)phenyl)-tert-butylphosphine)iridium, trihydride carbonylbis(4,4'-(phenylphosphinidene)bis(benzenesulfonic acid)dipotassium salt hydrate) iridium, trihydride carbonylbis((2-biphenyl)di-tert-butylphosphine)iridium, trihydride carbonylbis(2-di-tert-butylphosphino-2'-methylbiphenyl)iridium, trihydride carbonylbis(2-di-tert-butylphosphino-3,4,5,6-tetramethyl-2'4'6'-triisopropyl-1,1'-biphenyl)iridium, trihydride carbonylbis(2-di-tert-butylphosphino-2'4'6'-triisopropylbiphenyl) iridium, trihydride carbonylbis(di(1-adamantyl) benzylphosphine)iridium, trihydride carbonyl(dicyclohexyl(4-dimethylaminophenyl)phosphine) (tribenzylphosphine) iridium, trihydride carbonyl(dicyclohexyl(4-dimethylaminophenyl)phosphine) (triisopropylphosphine) iridium and trihydride carbonyl((4-dimethylaminophenyl) diphenylphosphine) (tribenzylphosphine)iridium.

The following are specific examples of the complex (1') which is a complex represented by $MH_m(CO)L_n$, wherein M represents rhodium, and the tri-substituted phosphine $PR^1R^2R^3$ as the ligand L has the substituents $R^1$, $R^2$ and $R^3$ at least one of which is neither an optionally substituted aromatic hydrocarbon group having from 6 to 15 carbons nor an optionally substituted alicyclic hydrocarbon group having from 5 to 10 carbons: trihydride carbonylbis(tribenzylphosphine)rhodium, trihydride carbonylbis(triisopropylphosphine)rhodium and trihydride carbonyl(dicyclohexyl(4-(N,N-dimethylamino)phenyl)phosphine) (tribenzylphosphine)rhodium.

The following are specific examples of the complex (1') which is a complex represented by $MH_m(CO)L_n$, wherein M represents iron, and the tri-substituted phosphine $PR^1R^2R^3$ as the ligand L has the substituents $R^1$, $R^2$ and $R^3$ at least one of which is neither an optionally substituted aromatic hydrocarbon group having from 6 to 15 carbons nor an optionally substituted alicyclic hydrocarbon group having from 5 to 10 carbons: dihydride carbonyl tris(dicyclohexyl(4-(N,N-dimethylamino)phenyl)phosphine)iron, dihydride carbonyl tris (tribenzylphosphine)iron, dihydride carbonyl tris(triisopropylphosphine)iron, dihydride carbonyl bis(dicyclohexyl(4-(N,N-dimethylamino)phenyl)phosphine) (tribenzylphosphine)iron, dihydride carbonyl(dicyclohexyl (4-(N,N-dimethylamino)phenyl)phosphine)bis(tribenzylphosphine)iron and dihydride carbonyl(dicyclohexyl(4-(N, N-dimethylamino)phenyl)phosphine) (tribenzyiphosphine) (triisopropylphosphine)iron.

The following are specific examples of the complex (1') which is a complex represented by $MH_m(CO)L_n$, wherein M represents ruthenium, and the tri-substituted phosphine $PR^1R^2R^3$ as the ligand L has the substituents $R^1$, $R^2$ and $R^3$ at least one of which is neither an optionally substituted aromatic hydrocarbon group having from 6 to 15 carbons nor an optionally substituted alicyclic hydrocarbon group having from 5 to 10 carbons: dihydride carbonyl tris(tribenzylphosphine) ruthenium, dihydride carbonyl tris(triisopropylphosphine)ruthenium, dihydride carbonyl bis(dicyclohexyl(4-(N,N-dimethylamino)phenyl)phosphine) (tribenzylphosphine)ruthenium, dihydride carbonyl(dicyclohexyl(4-(N,N-dimethylamino)phenyl)phosphine)bis (tribenzylphosphine)ruthenium and dihydride carbonyl(dicyclohexyl(4-(N,N-dimethylamino)phenyl)phosphine) (tribenzyiphosphine) (triisopropylphosphine)ruthenium.

<Method for Producing Metal Phosphine Complex>

A metal phosphine complex represented by General Formula (1) (i.e. complex (1)) can be produced by reacting a metal bidentate ligand complex represented by the General Formula (3) below (i.e. complex (3)) with a tri-substituted phosphine represented by the General Formula (2) (i.e. phosphine (2)) and hydrogen under appropriate conditions.

$$L^{10}{}_kL^{20}{}_2M \quad (3)$$

wherein in Formula (3), the definition of M is the same as in the Formula (1). In cases where M is an iridium or rhodium atom, k=1, and in cases where M is an iron or ruthenium atom, k=2.

$L^{10}$ represents a negative monovalent bidentate ligand. Representative examples of $L^{10}$ include acetylacetonato (abbreviated as acac) and phenoxyimine each of which may have a substituent(s). Examples of the substituent(s) include linear, branched and cyclic hydrocarbon groups having from 1 to 6 carbon atoms (e.g., methyl group and tert-butyl group), and aromatic hydrocarbon groups (e.g., phenyl group).

$L^{20}$s each independently represent a neutral ligand, or the two $L^{20}$s may together form a cyclic neutral ligand. The $L^{20}$s are not limited as long as the reaction for producing the complex (1) appropriately proceeds, and representative examples of the $L^{20}$s include cyclic neutral olefin ligands (e.g., 1,5-cyclooctadiene), which correspond to cyclic neutral ligands formed by the combination of the two $L^{20}$s. Alternatively, the $L^{20}$s may be acyclic olefin ligands (e.g., two molecules of ethylene) or phosphines other than the phosphine (2).

The hydrogen in the above reaction may be supplied from an appropriate reducing agent (hydrogen source). Representative examples of such a reducing agent include formic acid, and examples of the reducing agent also include other reducing agents such as isopropanol, methanol, ethanol, formaldehyde, sodium borohydride, potassium borohydride, triethylaluminum and ammonia, which are used for synthesis of common metal hydride complexes.

The above reaction is carried out by a mode appropriately selected depending on the phosphine (2) ligand from: [i] a mode in which the complex (3), phosphine (2) and hydrogen are reacted in a single stage; and [ii] a mode in which the complex (3) and phosphine (2) are reacted in an appropriate solvent, and the solvent is then removed, followed by reacting the produced intermediate (which corresponds to the later-mentioned complex (5)) with hydrogen. In cases where an inappropriate reaction mode is selected, the compound produced may be different from the compound of interest. For example, in cases where tris(4-methoxyphenyl)phosphine: $P(4-MeOPh)_3$ is used to synthesize an iridium hydride complex $IrH_3(CO)(P(4-MeOPh)_3)_2$, it is appropriate to select the reaction mode [ii](see the synthesis scheme in Example 1-2 described below), and, in cases where the reaction mode [i] is selected, the complex of interest may not be obtained. Conversely, for example, in cases where dicyclohexyl(4-dimethylaminophenyl)phosphine is used to synthesize an iridium hydride complex: $IrH_3(CO)(PCy_2(4-dmaPh))_2$, it is appropriate to select the reaction mode [i] (see the synthesis scheme in Example 1-1 described below), but the complex of interest may be obtained in some cases even in cases where the reaction mode [ii] is selected.

Representative examples of the solvent used in the reaction mode [ii] include 1,2-dimethoxyethane, methanol, ethanol, isopropanol, toluene, tetrahydrofuran, hexane, heptane, diethylether, N,N-dimethylformamide, dichloromethane, formic acid and water. These may also be used as a mixture containing them at arbitrary proportions.

In cases where M is iridium or rhodium, the complex (1) can be produced by reacting one molecule of the complex (3) with two molecules of the phosphine (2) (see the synthesis scheme in Example 1-2 described below). On the other hand, in cases where M is iron or ruthenium, the complex (1) can be produced by reacting one molecule of the complex (3) with three-molecules of the phosphine (2). By controlling the amounts of the complex (3) and the phosphine (2) used as raw materials depending on the stoichiometry, the complex (1) can be produced.

The temperature (heating) condition of the above reaction may be controlled within the range of usually 0 to 120° C., preferably 20 to 100° C., more preferably 55 to 80° C.

Here, in cases where M is iridium or rhodium, and one molecule of the complex (3) is reacted with three molecules of the phosphine (2); or in cases where M is iron or ruthenium, and one molecule of the complex (3) is reacted with four molecules of the phosphine (2); a metal phosphine complex represented by General Formula (4) (i.e. complex (4)), which is different from the complex (1), is produced (see the synthesis scheme in Reference Example 1-8 described below).

$$MH_mL_n \qquad (4)$$

wherein in Formula (4), the definitions of M, L, and $R^1$, $R^2$ and $R^3$ in the phosphine (2) as the L are the same as those in the Formula (1), and their explanations and examples are also the same as those described above in relation to Formula (1). In cases where M is an iridium or rhodium atom, m=3 and n=3, and in cases where M is an iron or ruthenium atom, m=2 and n=4.

That is, the metal phosphine complex (4) includes the metal phosphine complexes represented by the General Formulae (41) to (44) below. In General Formulae (41) to (44), the definitions of $L^1$, $L^2$, $L^3$ and $L^4$ are the same as that of L in General Formula (4), that is, L in General Formula (1).

$$IrH_3L^1L^2L^3 \qquad (41)$$

$$RhH_3L^1L^2L^3 \qquad (42)$$

$$FeH_2L^1L^2L^3L^4 \qquad (43)$$

$$RuH_2L^1L^2L^3L^4 \qquad (44)$$

The complex (4) described above can also be used in the present invention similarly to the complex (1), although the catalyst performance may be variable to some extent. That is, other aspects of the present invention can also provide a metal phosphine complex represented by General Formula (4), a catalyst for producing hydrogen by the formic acid decomposition reaction, which comprises as a constituent component the complex, a process of producing hydrogen using the catalyst, and the like.

Further, as a compound corresponding to an intermediate in the production method [ii] for the complexes (1) and (4), a metal phosphine complex represented by General Formula 5 (i.e. complex (5)) can also be produced.

$$L^{10}{}_kML_2 \qquad (5)$$

wherein in Formula (5), the definitions of M, L, and $R^1$, $R^2$ and $R^3$ in the phosphine (2) as the L are the same as those in the Formula (1), the definition of $L^{10}{}_k$ is the same as that in the Formula (3), and their more specific explanations and examples are also the same as those described above in relation to Formulae (1) and (3). In cases where M is an iridium or rhodium atom, k=1, and in cases where M is an iron or ruthenium atom, k=2.

That is, the metal phosphine complex (5) includes the metal phosphine complexes represented by the General Formulae (51) to (54) below. In General Formulae (51) to (54), the definitions of $L^1$ and $L^2$ are the same as that of L in General Formula (5), that is, L in General Formula (1).

$$L^{10}IrL^1L^2 \qquad (51)$$

$$L^{10}RhL^1L^2 \qquad (52)$$

$$L^{10}{}_2FeL^1L^2 \qquad (53)$$

$$L^{10}{}_2RuL^1L^2 \qquad (54)$$

The complex (5) described above can also be used in the present invention similarly to the complex (1), although the catalyst performance may be variable to some extent. That is, other aspects of the present invention can also provide a metal phosphine complex represented by General Formula (5), a catalyst for producing hydrogen by the formic acid decomposition reaction, which comprises as a constituent component the complex, a process of producing hydrogen using the catalyst, and the like.

<Catalyst for Producing Hydrogen>

The catalyst for producing hydrogen of the present invention comprises as a constituent component a metal phosphine complex represented by the General Formula (1) described above.

It is also possible to use, instead of the complex (1), the complex (4) or (5) to produce a catalyst for producing hydrogen comprising the complex as a constituent component.

The complex (1) may be used as it is as the catalyst, or may be used in combination with other constituting substances (e.g. a carrier) as required to provide the catalyst. In cases where the complex (1) is used as the catalyst, any single type of the complex may be used, or a combination of a plurality of types of the complex may be used in combination (as a mixture).

<Process of Producing Hydrogen>

The process of producing hydrogen of the present invention comprises the step of producing hydrogen (and carbon dioxide) from formic acid in the presence of the catalyst for producing hydrogen of the present invention described above. This step is carried out by contacting the catalyst for producing hydrogen of the present invention with formic acid under appropriate conditions to allow dehydrogenation of formic acid represented by the chemical equation below to proceed.

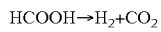

When the catalyst for producing hydrogen of the present invention is used, the dehydrogenation of formic acid proceeds also at room temperature, but the reaction rate (catalyst turnover frequency) can be increased by performing the reaction under heat at an appropriate temperature. The temperature upon the contact in the hydrogen-producing step of the present invention is adjusted within the range of usually 0 to 100° C., preferably 25 to 80° C.

Since the dehydrogenation of formic acid usually requires an appropriate amount of water, formic acid is mixed with water to prepare an aqueous formic acid solution having an appropriate concentration, and the prepared solution is used for the reaction step. The concentration of formic acid in the aqueous formic acid solution upon the contact is not limited, and is adjusted usually within the range of not less than 1% by volume to less than 100% by volume in consideration of the production efficiency of hydrogen (catalyst turnover frequency) and the like. The lower limit is preferably 20% by volume, more preferably 40% by volume, still more preferably 50% by volume, and the upper limit is preferably 98% by volume.

The amount of the catalyst for producing hydrogen to be used is not limited, and may be adjusted such that the concentration of the metal phosphine complex in the formic acid solution upon the contact is usually 0.01 to 500 μmol/mL, preferably 10 to 100 μmol/mL, in consideration of conditions such as the concentration of the aqueous formic acid solution.

In the process of producing hydrogen using the catalyst for producing hydrogen of the present invention, amine or phosphine, which has been sometimes used in combination with a conventional catalyst (see, for example, Non-patent Document 1), is not necessary, but, in order to further increase the reaction rate (catalyst turnover frequency) in the presence of formic acid in a high concentration range (for example, at 98% by volume), amine or phosphine may be used in combination. That is, the catalyst for producing hydrogen of the present invention may further contain amine or phosphine as a constituent component.

As the amine or phosphine, known compounds may be used. Examples of the amine include aliphatic amines, alicyclic amines, aromatic amines and heterocyclic amines, and specific examples thereof include N,N-dimethylaniline, triethylamine, diethylamine, butylamine, pyridine, bipyrimidine, N,N-dimethylaminopyridine and imidazole. On the other hand, examples of the phosphine include trialiphatic phosphine, trialicyclic phosphine, triaromatic phosphine and triaralkyl phosphine, and specific examples thereof include tributylphosphine.

The amount of the amine or phosphine to be added may be adjusted appropriately depending on its type, and is within the range of usually 1 to $10 \times 10^5$ μmol/mL, preferably 100 to 1000 μmol/mL.

Since hydrogen generated by the reaction as described above contains carbon dioxide as a by-product, the process of producing hydrogen of the present invention may further comprise a step wherein carbon dioxide is separated in order to enable use of high-purity hydrogen.

<Catalyst for Hydrogenation Reactions>

A catalyst having the same mode as the above-described catalyst for producing hydrogen of the present invention can also be used as a catalyst for hydrogenation reactions. That is, the catalyst for hydrogenation reactions of the present invention may comprise a metal phosphine complex represented by the General Formula (1) as a constituent component and further comprise the amine or phosphine.

<Method of Hydrogenation>

The method of hydrogenation of the present invention comprises the step of reacting an unsaturated compound with hydrogen in the presence of the catalyst for hydrogenation reactions of the present invention as described above and an aqueous formic acid solution.

Examples of the unsaturated compound include various compounds that can be subjects of common hydrogenation reactions and have at least one unsaturated bond in the molecule. For example, an unsaturated compound having a carbon-carbon double bond or carbon-carbon triple bond such as a linear or cyclic alkene or alkyne is a subject to which the hydrogenation reaction of the present invention is preferably applied. Further, it may be possible to apply the hydrogenation reaction of the present invention to a compound having a carbon-oxygen unsaturated bond, such as an aldehyde, ketone, carboxylic acid or carboxylic acid ester.

In the hydrogenation reaction by the present invention, the catalyst for hydrogenation reactions of the present invention may be brought into contact with an aqueous formic acid solution and an unsaturated compound under appropriate conditions. In this hydrogenation reaction, hydrogen derived from formic acid by the contact between the catalyst for hydrogenation reactions and the aqueous formic acid solution is reacted with an unsaturated bond in the unsaturated compound. That is, in the hydrogenation reaction of the present invention, formic acid (an aqueous solution) may be used as a source of hydrogen.

The concentration of the aqueous formic acid solution used in the hydrogenation reaction may be about the same as that in the above-described process of producing hydrogen, and is adjusted usually within the range of not less than 1% by volume to less than 100% by volume. The lower limit is preferably 5% by volume, more preferably 10% by volume, still more preferably 20% by volume, and the upper limit is preferably 98% by volume. In order to dissolve the unsaturated compound as the subject of hydrogenation reaction, an appropriate organic solvent compatible with the aqueous formic acid solution may be added as required. In this case, the concentration of the aqueous formic acid solution corresponds to the concentration of formic acid in the mixed solvent composed of the aqueous formic acid solution and the organic solvent added.

The hydrogenation reaction proceeds also at room temperature, but the reaction rate (catalyst turnover frequency) can be increased by performing the reaction under heat at an appropriate temperature. The temperature upon the contact in the hydrogenation step of the present invention is adjusted within the range of usually 0 to 100° C., preferably 20 to 80° C.

The amount of the catalyst for hydrogenation reactions to be used may be adjusted such that the concentration of the metal phosphine complex in the mixture upon the contact is usually 0.01 to 500 μmol/mL, preferably 10 to 100 μmol/mL, and the amount may be further adjusted depending on the concentration of the unsaturated compound in the mixture.

<Catalyst for Producing Formic Acid and Method for Producing Formic Acid>

The metal phosphine complex represented by General Formula (1) or the like used for the catalyst for producing hydrogen and the catalyst for hydrogenation reactions of the present invention may also be used for a catalyst for production of formic acid. That is, other aspects of the present invention provide a catalyst for producing formic acid, which comprises as a constituent component a metal phosphine complex represented by General Formula (1) or the like, and a method for producing formic acid, which comprises the step of producing formic acid from hydrogen and carbon dioxide in the presence of the catalyst. This step is carried out by contacting the catalyst for producing formic acid of the present invention with hydrogen and carbon dioxide under appropriate conditions to allow the reaction represented by the chemical equation below to proceed.

$$H_2 + CO_2 \rightarrow HCOOH$$

The temperature upon the contact in the above formic acid production step is adjusted within the range of usually 0 to 200° C., preferably 40 to 200° C. The pressure upon the contact (total pressure in the reaction system) is adjusted within the range of usually 1 to 100 atm, preferably 1 to 70 atm. The amount of the catalyst for producing formic acid to be used is adjusted such that the concentration of the metal phosphine complex in the reaction system upon the contact is within the range of usually 0.001 to 100 μmol/mL, preferably 0.01 to 100 μmol/mL.

<Fuel Cell>

The process of producing hydrogen of the present invention may be applied to various devices and apparatuses utilizing hydrogen gas, and the subject is not limited. In view of the excellent performance of the catalyst for producing hydrogen of the present invention, the process of producing hydrogen has excellent applicability to, for example, fuel cells. A fuel cell comprising as a constituent component the catalyst for producing hydrogen of the present invention can be produced in the same manner as a fuel cell in which a conventional catalyst for producing hydrogen is used, except that the catalyst for producing hydrogen of the present invention is used instead of the conventional catalyst for producing hydrogen and appropriate modifications are added as required.

EXAMPLES

Synthesis of Iridium Hydride Complex $IrH_3L_3$ or $IrH_3(CO)L_2$

The chemical structures of the iridium hydride complexes A to H synthesized in the experiment examples below and the ligands a to h, respectively, contained therein; and the chemical structures of known iridium hydride complexes I to J and the ligands i to j, respectively, contained therein; are as shown in the table below. The iridium hydride complexes A, B and E are complexes satisfying the definition of Formula (1), and the other iridium hydride complexes are complexes as reference examples which do not satisfy the definition of Formula (1).

TABLE 1

Iridium hydride complex A
$IrH_3(CO)(PCy_2(4\text{-dmaPh}))_2$

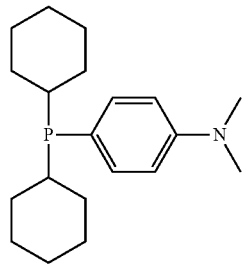 [SMILES: CN(C)c1ccc(P(C2CCCCC2)C2CCCCC2)cc1]

Ligand a

Iridium hydride complex B
$IrH_3(CO)(P(4\text{-MeOPh})_3)_2$

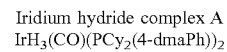

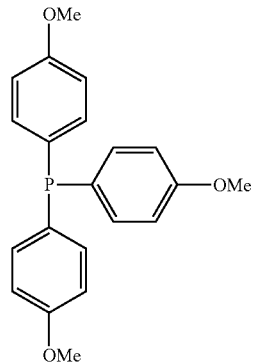 [SMILES: COc1ccc(P(c2ccc(OC)cc2)c2ccc(OC)cc2)cc1]

Ligand b

Iridium hydride complex C
$IrH_3(CO)(P(3\text{-}SO_3NaPh)_3)_2$

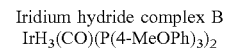

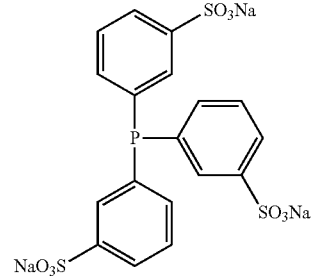

Ligand c

TABLE 1-continued

Iridium hydride complex D
IrH$_3$(PPh$_2$(C$_6$F$_5$))$_3$

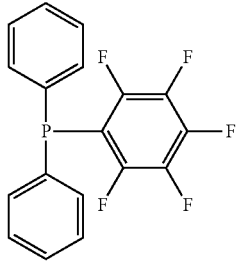 [SMILES: Fc1c(F)c(F)c(P(c2ccccc2)c2ccccc2)c(F)c1F]

Ligand d

Iridium hydride complex E
IrH$_3$(CO)(P(4-dmaPh)Ph$_2$)$_2$

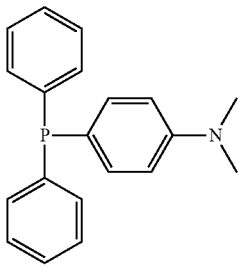 [SMILES: CN(C)c1ccc(P(c2ccccc2)c2ccccc2)cc1]

Ligand e

Iridium hydride complex F
IrH$_3$(CO)(PiPr$_3$)$_2$

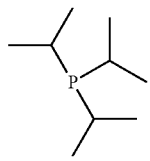

Ligand f

Iridium hydride complex G
IrH$_3$(CO)(PBz$_3$)$_2$

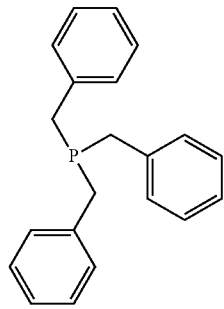 [SMILES: c1ccc(CP(Cc2ccccc2)Cc2ccccc2)cc1]

Ligand g

TABLE 1-continued

Iridium hydride complex H
IrH$_3$(P(4-MeOPh)$_3$)$_3$

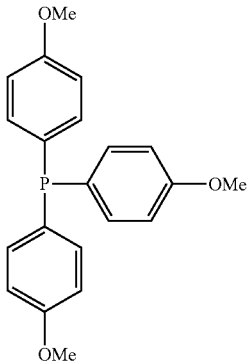 [SMILES: COc1ccc(P(c2ccc(OC)cc2)c2ccc(OC)cc2)cc1]

Ligand h

Iridium hydride complex I
IrH$_3$(CO)(PPh$_3$)$_2$

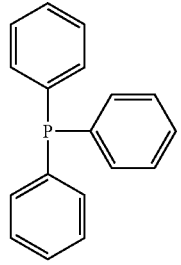 [SMILES: c1ccc(P(c2ccccc2)c2ccccc2)cc1]

Iridium hydride complex J
IrH$_3$(CO)(PCy$_3$)$_2$

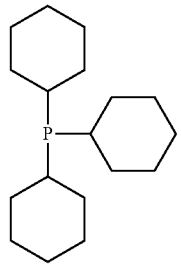 [SMILES: C1CCC(P(C2CCCCC2)C2CCCCC2)CC1]

Example 1-1

Synthesis of Iridium Hydride Complex A (IrH$_3$(CO)(PCy$_2$(4-dmaPh))$_2$) (See the Synthesis Scheme Below)

Under argon atmosphere, dicyclohexyl(4-dimethylaminophenyl)phosphine (a) (95.2 mg, 0.30 mmol) and acetylacetonato iridium (1,5-cyclooctadiene) (20.0 mg, 0.05 mmol) were placed in a Schlenk flask. Two milliliters of a degassed aqueous formic acid solution (98 vol %) was added thereto with a syringe, and the flask was tightly sealed, followed by stirring the resulting mixture at 60° C. for 1 hour. Thereafter, the aqueous formic acid solution was removed under reduced pressure, and the resultant was washed with ethanol, to obtain the iridium hydride complex A as pale yellow powder (32.9 mg, 0.04 mmol).

[Chemical Formula 1]

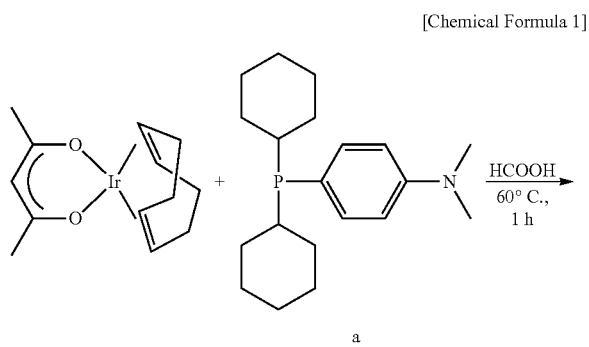

a

Example 1-2

Synthesis of Iridium Hydride Complex B (IrH$_3$(CO)(P(4-MeOPh)$_3$)$_2$) (See the Synthesis Scheme Below)

Under argon atmosphere, tris(4-methoxyphenyl)phosphine (b) (35.2 mg, 0.10 mmol) and acetylacetonato iridium (1,5-cyclooctadiene) (20.0 mg, 0.05 mmol) were placed in a Schlenk flask. One milliliter of a degassed 1,2-dimethoxyethane was added thereto with a syringe, and the flask was tightly sealed, followed by stirring the resulting mixture at 80° C. for 3.5 hours. Thereafter, 1,2-dimethoxyethane was removed under reduced pressure, and 0.5 mL of a degassed aqueous formic acid solution (98 vol %) was added thereto with a syringe. The flask was tightly sealed, and the mixture was stirred at 60° C. for 1 hour. Thereafter, the aqueous formic acid solution was removed under reduced pressure, and ethanol was added thereto, followed by stirring the resulting mixture overnight and then washing. As a result, the iridium hydride complex B was obtained as white powder (8.8 mg, 0.01 mmol).

[Chemical Formula 2]

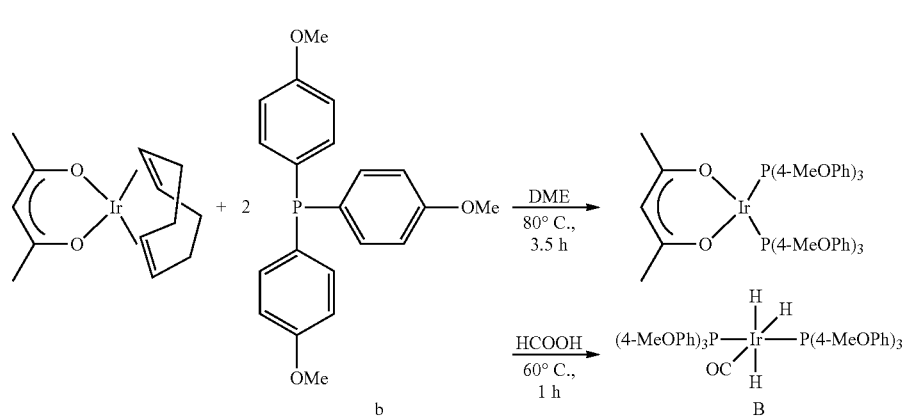

b

-continued

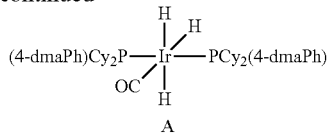

A

Spectroscopic Data of the Iridium Hydride Complex A (See FIG. 1 to FIG. 4):

$^1$H NMR (CD$_2$Cl$_2$), δ: 7.76-7.81 (m, 4H), 6.69-6.71 (m, 4H), 2.97 (s, 12H), 1.07-2.08 (m, 44H), [mer: −11.33 (td, 2H), −12.66 (tt, 1H)]

$^{31}$P[$^1$H] NMR (CD$_2$Cl$_2$), δ: 28.4 (s)

$^{13}$C NMR (CD$_2$Cl$_2$), δ: 179.5 (CO)

IR (Nujol, cm$^{-1}$), ν: 2081, 2036, 1953, 1934, 1776 (IrH, CO)

Spectroscopic Data of the Iridium Hydride Complex B:

$^1$H NMR (C$_6$D$_6$), δ: 7.60-8.10 (m, 12H), 6.62-6.78 (m, 12H), 3.23 (s, 18H), [mer: −9.03 (td, J$_{H-P}$=16.8 Hz, J$_{H-H}$=4.4 Hz, 2H), −9.61 (tt, J$_{H-P}$=19.6 Hz, J$_{H-H}$=4.4 Hz, 1H)], [fac: −9.24 (t, J$_{H-P}$=18.4 Hz, 1H), −10.41 (ddd, J$_{H-P}$=105.5, 17.6 Hz, J$_{H-H}$=2.0 Hz, 2H)]

$^{31}$P[$^1$H] NMR (CD$_2$Cl$_2$), δ: [mer: 9.16 (s)], [fac: 1.37 (s)]

Reference Example 1-3

Synthesis of Iridium Hydride Complex C (IrH$_3$(CO)(P(3-SO$_3$NaPh)$_3$)$_2$)

Under argon atmosphere, tris(3-sulfonatophenyl)phosphine hydrate sodium salt (c) (42.6 mg, 0.075 mmol) and acetylacetonato iridium(1,5-cyclooctadiene) (10.0 mg, 0.025 mmol) were placed in a Schlenk flask. One-half milliliters of a degassed aqueous formic acid solution (98 vol %) was added thereto with a syringe, and the flask was tightly sealed, followed by stirring the resulting mixture at 60° C. for 1 hour. Thereafter, the aqueous formic acid solution was removed under reduced pressure, and the resultant was washed with ethanol, to obtain the iridium hydride complex C as white powder (46.6 mg).

Spectroscopic Data of the Iridium Hydride Complex C:

$^1$H NMR (D$_2$O), δ: 6.97-8.00 (m, 24H), [fac: −10.64 (t, $J_{H-P}$=18.4 Hz, 1H), −11.83 (ddd, $J_{H-P}$=102.7, 20.4 Hz, $J_{H-H}$=4.8 Hz, 2H)]

Reference Example 1-4

Synthesis of Iridium Hydride Complex D (IrH$_3$(PPh$_2$(C$_6$F$_5$))$_3$)

Under argon atmosphere, diphenyl(pentafluorophenyl)phosphine (d) (52.8 mg, 0.15 mmol) and acetylacetonato iridium (1,5-cyclooctadiene) (20.0 mg, 0.05 mmol) were placed in a Schlenk flask. One milliliter of a degassed 1,2-dimethoxyethane was added thereto with a syringe, and the flask was tightly sealed, followed by stirring the resulting mixture at 80° C. for 3.5 hours. Thereafter, 1,2-dimethoxyethane was removed under reduced pressure, and 0.5 mL of a degassed aqueous formic acid solution (98 vol %) was added thereto with a syringe. The flask was tightly sealed, and the mixture was stirred at 60° C. for 15 minutes. Thereafter, the aqueous formic acid solution was removed under reduced pressure, and the resultant was washed with ethanol, to obtain the iridium hydride complex D as white powder (23.9 mg, 0.02 mmol).

Spectroscopic Data of the Iridium Hydride Complex D:

$^1$H NMR (CD$_2$Cl$_2$), δ: 7.58-7.60 (m, 12H), 7.20-7.23 (m, 18H), [fac: −12.18 (dd, $J_{H-P}$=85.5 Hz, $J_{H-P}$=20.4 Hz, 3H)]

$^{31}$P[$^1$H] NMR (CD$_2$Cl$_2$), δ: 2.97 (s)

Example 1-5

Synthesis of Iridium Hydride Complex E (IrH$_3$(CO)(P (4-dmaPh) Ph$_2$)$_2$)

Under argon atmosphere, (4-dimethylaminophenyl)diphenylphosphine (e) (122.1 mg, 0.4 mmol) and acetylacetonato iridium(1,5-cyclooctadiene) (80.0 mg, 0.2 mmol) were placed in a Schlenk flask. Four milliliters of a degassed 1,2-dimethoxyethane was added thereto with a syringe, and the flask was tightly sealed, followed by stirring the resulting mixture at 15° C. for 12 hours. Thereafter, 1,2-dimethoxyethane was removed under reduced pressure, and 2.5 mL of a degassed aqueous formic acid solution (98 vol %) was added thereto with a syringe. The flask was tightly sealed, and the mixture was stirred at 60° C. for 1 hour. Thereafter, the aqueous formic acid solution was removed under reduced pressure, and ethanol was added thereto, followed by stirring the resulting mixture overnight and then washing. As a result, the iridium hydride complex E was obtained as white powder (115.9 mg, 0.14 mmol).

Spectroscopic Data of the Iridium Hydride Complex E:

$^1$H NMR (CD$_2$Cl$_2$), δ: 7.17-7.68 (m, 24H), 6.51-6.53 (m, 4H), 2.99 (s, 12H), [mer: −10.08 (td, $J_{H-P}$=16.8 Hz, $J_{H-H}$=4.8 HZ, 2H), −10.48 (tt, $J_{H-P}$=18.8 Hz, $J_{H-H}$=5.2 Hz, 1H)], [fac: −10.18 (t, $J_{H-P}$=18.4 Hz, 1H), −11.64 (ddd, $J_{H-P}$=103.5, 19.2 Hz, $J_{H-H}$=2.4 Hz, 2H)]

$^{31}$P[$^1$H] NMR (CD$_2$Cl$_2$), δ: [mer: 13.9 (s)], [fac: 5.62 (s)]

Reference Example 1-6

Synthesis of Iridium Hydride Complex F(IrH$_3$(CO)(PiPr$_3$)$_2$)

Under argon atmosphere, triisopropylphosphine (f) (172 µL, 0.90 mmol) and acetylacetonato iridium(1,5-cyclooctadiene) (120.0 mg, 0.30 mmol) were placed in a Schlenk flask. Three milliliter of a degassed aqueous formic acid solution (98 vol %) was added thereto with a syringe, and the flask was tightly sealed, followed by stirring the resulting mixture at 60° C. for 3 minutes. Thereafter, the aqueous formic acid solution was removed under reduced pressure, and the resultant was washed with ethanol, to obtain the iridium hydride complex F as yellow powder (26.5 mg)

Spectroscopic Data of the Iridium Hydride Complex F:

$^1$H NMR (CD$_2$Cl$_2$), δ: 2.00 (m, 6H), 1.17 (m, 36H), [mer: −12.16 (td, $J_{H-P}$=15.2 Hz, $J_{H-H}$=4.8 Hz, 2H), −12.97 (tt, $J_{H-P}$=19.2 Hz, $J_{H-H}$=4.8 Hz, 1H)]

$^{31}$P[$^1$H] NMR (CD$_2$Cl$_2$), δ: 41.7 (s)

Reference Example 1-7

Synthesis of Iridium Hydride Complex G (IrH$_3$(CO)(PBz$_3$)$_2$)

Under argon atmosphere, tribenzylphosphine (g) (45.7 mg, 0.15 mmol) and acetylacetonato iridium (1,5-cyclooctadiene) (20.0 mg, 0.05 mmol) were placed in a Schlenk flask. One milliliter of a degassed 1,2-dimethoxyethane was added thereto with a syringe, and the flask was tightly sealed, followed by stirring the resulting mixture at 80° C. for 3.5 hours. Thereafter, 1,2-dimethoxyethane was removed under reduced pressure, and 1.5 mL of a degassed aqueous formic acid solution (98 vol %) was added thereto with a syringe. The flask was tightly sealed, and the mixture was stirred at 60° C. for 1 hour. Thereafter, the aqueous formic acid solution was removed under reduced pressure, and the resultant was washed with ethanol, to obtain the iridium hydride complex G as white powder (28.2 mg, 0.03 mmol).

Spectroscopic Data of the Iridium Hydride Complex G:

$^1$H NMR (CD$_2$Cl$_2$), δ:7.05-7.27 (m, 30H), 3.25 (s, 12H), [mer: −11.80 (td, $J_{H-P}$=16.8 Hz, $J_{H-H}$=4.8 Hz, 2H), −11.99 (tt, $J_{H-P}$=20.0 Hz, $J_{H-H}$=4.8 Hz, 1H)]

$^{31}$P[$^1$H] NMR (CD$_2$Cl$_2$), δ: 6.63 (s)

Reference Example 1-8

Synthesis of Iridium Hydride Complex H (IrH$_3$(P (4-MeOPh)$_3$)$_3$) (See the Synthesis Scheme Described Below)

Under argon atmosphere, tris(4-methoxyphenyl)phosphine (b) (52.9 mg, 0.15 mmol) and acetylacetonato iridium (1,5-cyclooctadiene) (20.0 mg, 0.05 mmol) were placed in a Schlenk flask. One milliliter of a degassed 1,2-dimethoxyethane was added thereto with a syringe, and the flask was tightly sealed, followed by stirring the resulting mixture at 80° C. for 3.5 hours. Thereafter, 1,2-dimethoxyethane was removed under reduced pressure, and 0.5 mL of a degassed aqueous formic acid solution (98 vol %) was added thereto with a syringe. The flask was tightly sealed, and the mixture was stirred at 60° C. for 1 hour. Thereafter, the aqueous formic acid solution was removed under reduced pressure, and the resultant was washed with ethanol, to obtain the iridium hydride complex H as white powder (38.9 mg, 0.03 mmol)

Spectroscopic Data of the Iridium Hydride Complex H:

$^1$H NMR (CD$_2$Cl$_2$), δ: 6.85-7.19 (m, 18H), 6.38-6.68 (m, 18H), 3.72 (s, 27H), [mer: −11.1 (q, $J_{H-P}$=23.6 Hz, 3H)]

$^{31}$P[$^1$H] NMR (CD$_2$Cl$_2$), δ: 14.12 (d)

[Chemical Formula 3]

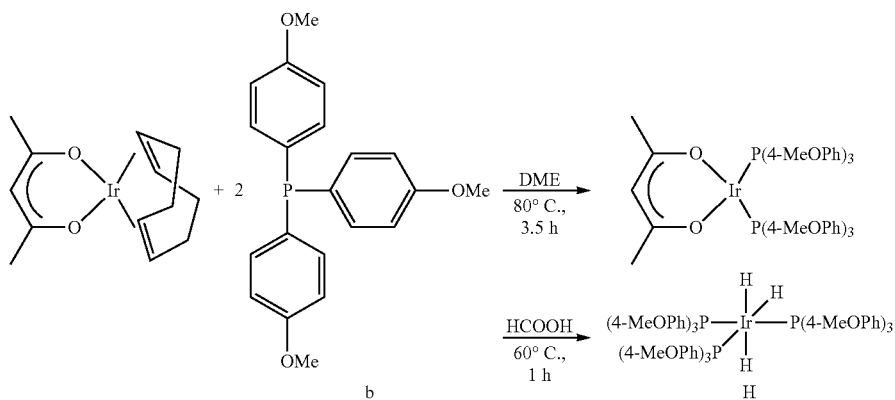

b

Formic Acid Decomposition Reaction Using Iridium Hydride Complex: $IrH_3L_3$ or $IrH_3(CO)L_2$ Examples/Reference Examples 2-1 to 2-10

Under argon atmosphere, a predetermined amount of each of the iridium hydride complexes (A, B, C, D, E, F, G and H) and an aqueous formic acid solution (98 vol %, 0.095 mL) were placed in a glass test tube, and the test tube was sealed with a septum. The total weight of the test tube was measured, and the test tube was heated at 60° C. for 1 hour. In this reaction, the septum was punctured with a syringe needle to allow generated hydrogen and carbon dioxide to escape to the outside, to keep the pressure inside the test tube constant. After the reaction, the weight of the test tube was measured, and the catalyst turnover frequency was calculated based on the amount of decrease in the weight. Further, the same experiment as described above was carried out using, as a catalyst for the formic acid decomposition reaction, a known iridium hydride complex $IrH_3(CO)(PPh_3)_2$ (Complex I) having triphenylphosphine ($PPh_3$) as the ligand or $IrH_3(CO)(PCy_3)_2$ (Complex J) having tricyclohexylphosphine ($PCy_3$) as the ligand. The results for Examples/Reference Examples 2-1 to 2-10 are shown in Table 2.

TABLE 2

Formic Acid Decomposition Reaction Using Iridium Hydride Complex

| Example/Reference Example | Catalyst | Amount of catalyst (μmol) | Aqueous formic acid solution (mL) | Aqueous formic acid solution (vol. %) | Reaction temperature (° C.) | Reaction time (h) | Catalyst turnover frequency ($h^{-1}$) |
|---|---|---|---|---|---|---|---|
| 2-1 | A | 1.6 | 0.095 | 98 | 60 | 1 | 4000 |
| 2-2 | B | 1.6 | 0.095 | 98 | 60 | 1 | 110 |
| 2-3 | C | 1.4 | 0.095 | 98 | 60 | 1 | 70 |
| 2-4 | D | 1.2 | 0.095 | 98 | 60 | 1 | 70 |
| 2-5 | E | 1.6 | 0.095 | 98 | 60 | 1 | 950 |
| 2-6 | F | 1.6 | 0.095 | 98 | 60 | 1 | 260 |
| 2-7 | G | 1.6 | 0.095 | 98 | 60 | 1 | 450 |
| 2-8 | H | 1.6 | 0.095 | 98 | 60 | 1 | 90 |
| 2-9 | I | 1.6 | 0.095 | 98 | 60 | 1 | 420 |
| 2-10 | J | 1.6 | 0.095 | 98 | 60 | 1 | 1000 |

Examples 3-1 to 3-7

Under argon atmosphere, the iridium hydride complex A (2.2 mg, 2.0 μmol) and an aqueous formic acid solution at a predetermined concentration (10 mL) were placed in a Schlenk flask, and the flask was sealed with a glass stopper. The total weight of the Schlenk flask was measured, and the Schlenk flask was heated at 60° C. for 1 hour. In this reaction, the cock of the Schlenk flask was opened to allow generated hydrogen and carbon dioxide to escape to the outside, to keep the pressure inside the Schlenk flask constant. After the reaction, the weight of the Schlenk flask was measured, and the catalyst turnover frequency was calculated based on the amount of decrease in the weight. The results for Examples 3-1 to 3-7 are shown in Table 3.

TABLE 3

Influence of Formic Acid Concentration on Formic Acid Decomposition Reaction

| Example | Catalyst | Amount of catalyst (μmol) | Aqueous formic acid solution (mL) | Aqueous formic acid solution (vol. %) | Reaction temperature (° C.) | Reaction time (h) | Catalyst turnover frequency (h$^{-1}$) |
|---|---|---|---|---|---|---|---|
| 3-1 | A | 2.0 | 10 | 20 | 60 | 1 | 1 |
| 3-2 | A | 2.0 | 10 | 30 | 60 | 1 | 50 |
| 3-3 | A | 2.0 | 10 | 40 | 60 | 1 | 2600 |
| 3-4 | A | 2.0 | 10 | 50 | 60 | 1 | 2800 |
| 3-5 | A | 2.0 | 10 | 60 | 60 | 1 | 2800 |
| 3-6 | A | 2.0 | 10 | 70 | 60 | 1 | 2200 |
| 3-7 | A | 2.0 | 10 | 80 | 60 | 1 | 580 |

Examples 4-1 to 4-6

Figure 5:
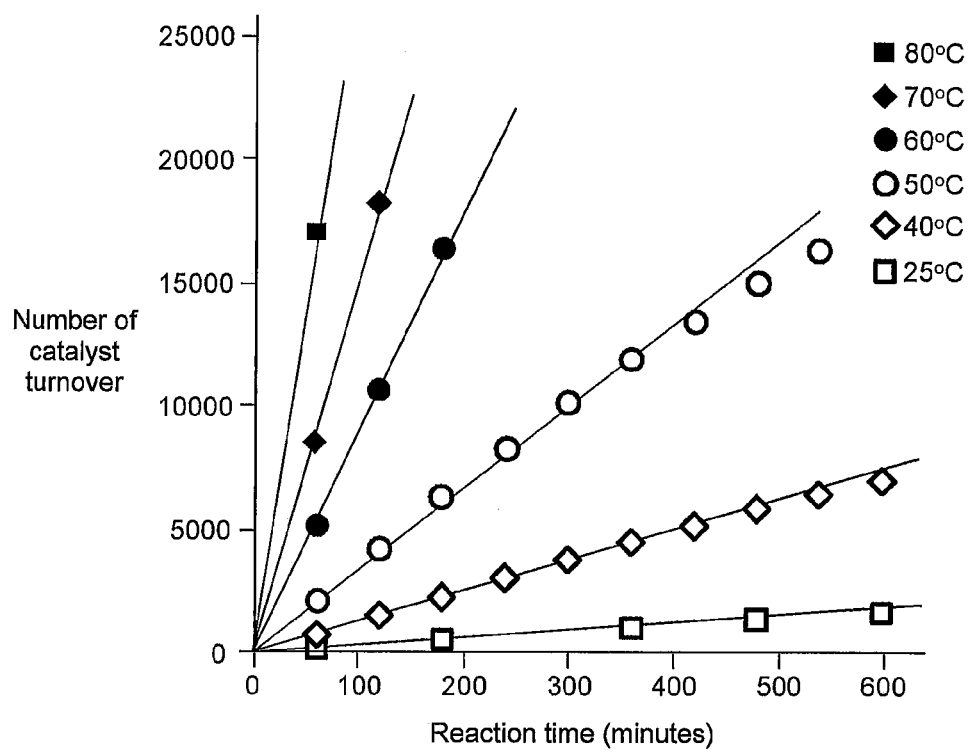
FIG. 5 shows the influence of the reaction temperature on the formic acid decomposition reaction (change with time; the reaction conditions were the same as in Table 4)

Under argon atmosphere, the iridium hydride complex A (1.4 mg, 1.6 μmol) and aqueous formic acid solution (60 vol %, 2.5 mL) were placed in a glass test tube, and the test tube was sealed with a septum. The total weight of the test tube was measured, and the test tube was heated at a predetermined temperature for 1 hour. In this reaction, the septum was punctured with a syringe needle to allow generated hydrogen and carbon dioxide to escape to the outside, to keep the pressure inside the test tube constant. After the reaction, the weight of the test tube was measured, and the catalyst turnover frequency was calculated based on the amount of decrease in the weight. The results for Examples 4-1 to 4-6 are shown in Table 4 and FIG. 5.

TABLE 4

Influence of Reaction Temperature on Formic Acid Decomposition Reaction

| Example | Catalyst | Amount of catalyst (μmol) | Aqueous formic acid solution (mL) | Aqueous formic acid solution (vol. %) | Reaction temperature (° C.) | Reaction time (h) | Catalyst turnover frequency (h$^{-1}$) |
|---|---|---|---|---|---|---|---|
| 4-1 | A | 1.6 | 2.5 | 60 | 25 | 1 | 180 |
| 4-2 | A | 1.6 | 2.5 | 60 | 40 | 1 | 730 |
| 4-3 | A | 1.6 | 2.5 | 60 | 50 | 1 | 2100 |
| 4-4 | A | 1.6 | 2.5 | 60 | 60 | 1 | 5100 |
| 4-5 | A | 1.6 | 2.5 | 60 | 70 | 1 | 8500 |
| 4-6 | A | 1.6 | 2.5 | 60 | 80 | 1 | 17000 |

Examples 5-1 to 5-4

Under argon atmosphere, the iridium hydride complex A (1.4 mg, 1.6 μmol) and a predetermined amount of an aqueous formic acid solution (98 vol %) were placed in a glass test tube, and the test tube was sealed with a septum. The total weight of the test tube was measured, and the test tube was heated at 60° C. for 1 hour. In this reaction, the septum was punctured with a syringe needle to allow generated hydrogen and carbon dioxide to escape to the outside, to keep the pressure inside the test tube constant. After the reaction, the weight of the test tube was measured, and the catalyst turnover frequency was calculated based on the amount of decrease in the weight. The results for Examples 5-1 to 5-4 are shown in Table 5.

TABLE 5

Influence of Catalyst Concentration on Formic Acid Decomposition Reaction

| Example | Catalyst | Amount of catalyst (μmol) | Aqueous formic acid solution (mL) | Aqueous formic acid solution (vol. %) | Reaction temperature (° C.) | Reaction time (h) | Catalyst turnover frequency (h$^{-1}$) |
|---|---|---|---|---|---|---|---|
| 5-1 | A | 1.6 | 0.095 | 98 | 60 | 1 | 4000 |
| 5-2 | A | 1.6 | 0.500 | 98 | 60 | 1 | 2800 |
| 5-3 | A | 1.6 | 1.000 | 98 | 60 | 1 | 2000 |
| 5-4 | A | 1.6 | 2.000 | 98 | 60 | 1 | 1300 |

Examples 6-1 to 6-9

Under argon atmosphere, the iridium hydride complex A (1.4 mg, 1.6 μmol), an aqueous formic acid solution (98 vol %, 1.0 mL) and a predetermined amount of an additive were placed in a glass test tube, and the test tube was sealed with a septum. The total weight of the test tube was measured, and the test tube was heated at 60° C. for 1 hour. In this reaction, the septum was punctured with a syringe needle to allow generated hydrogen and carbon dioxide to escape to the outside, to keep the pressure inside the test tube constant. After the reaction, the weight of the test tube was measured, and the catalyst turnover frequency was calculated based on the amount of decrease in the weight. The results for Examples 6-1 to 6-9 are shown in Table 6.

TABLE 6

Influence of Additives on Formic Acid Decomposition Reaction

| Example | Catalyst | Amount of catalyst (μmol) | Aqueous formic acid solution (mL) | (vol. %) | Additive | Amount of additive (μmol) | Reaction temperature (° C.) | Reaction time (h) | Catalyst turnover frequency ($h^{-1}$) |
|---|---|---|---|---|---|---|---|---|---|
| 6-1 | A | 1.6 | 1.0 | 98 | — | — | 60 | 1 | 2000 |
| 6-2 | A | 1.6 | 1.0 | 98 | N,N-Dimethyl aniline | 0.1 | 60 | 1 | 2300 |
| 6-3 | A | 1.6 | 1.0 | 98 | N,N-Dimethyl aniline | 1.0 | 60 | 1 | 4000 |
| 6-4 | A | 1.6 | 1.0 | 98 | Triethylamine | 1.0 | 60 | 1 | 3700 |
| 6-5 | A | 1.6 | 1.0 | 98 | Diethylamine | 1.0 | 60 | 1 | 3600 |
| 6-6 | A | 1.6 | 1.0 | 98 | Butylamine | 1.0 | 60 | 1 | 3400 |
| 6-7 | A | 1.6 | 1.0 | 98 | Pyridine | 1.0 | 60 | 1 | 1800 |
| 6-8 | A | 1.6 | 1.0 | 98 | Bipyrimidine | 1.0 | 60 | 1 | 590 |
| 6-9 | A | 1.6 | 1.0 | 98 | Tributylphosphine | 1.0 | 60 | 1 | 1100 |

Synthesis of Iridium Complex: $Ir(acac)L_2$

The chemical structures of the iridium complexes A to I synthesized in the experiment examples below and their respective ligands a to h are as shown in Table 7. It should be noted that these iridium complexes are complexes as reference examples, which do not satisfy the definition of Formula (1).

TABLE 7

Hydride complex A
$Ir(acac)(P(4-MeOPh)_3)_2$

Ligand a

TABLE 7-continued
Hydride complex B
Ir(acac)(P(4-dmaPh)Ph₂)₂
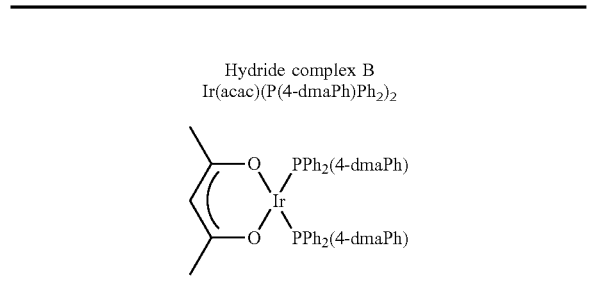
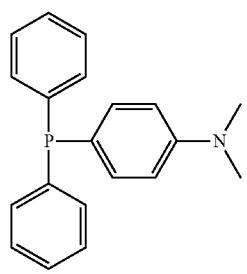 [SMILES: CN(C)c1ccc(P(c2ccccc2)c2ccccc2)cc1]
Ligand b
Hydride complex C
Ir(acac)(PPh₃(4-MePh))₂
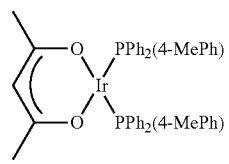
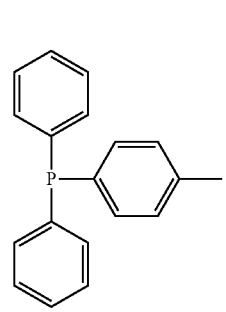 [SMILES: Cc1ccc(P(c2ccccc2)c2ccccc2)cc1]
Ligand c
Hydride complex D
Ir(acac)(PCy₃)₂
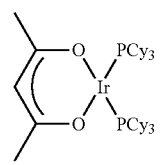
TABLE 7-continued
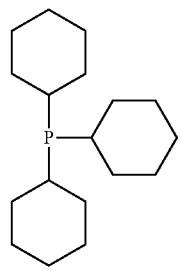 [SMILES: C1CCC(P(C2CCCCC2)C2CCCCC2)CC1]
Ligand d
Hydride complex E
Ir(acac)(PBu₃)₂
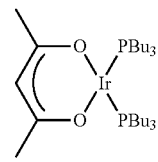
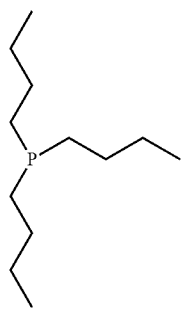
Ligand e
Hydride complex F
Ir(acac)(dppe)
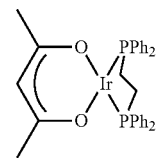
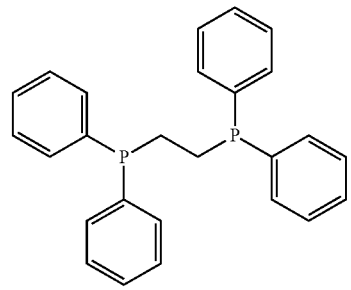 [SMILES: c1ccc(P(CCP(c2ccccc2)c2ccccc2)c2ccccc2)cc1]
Ligand f TABLE 7-continued Hydride complex G
Ir(acac-Ph₂)(PPh₃)₂

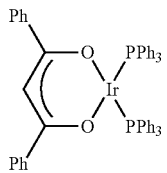

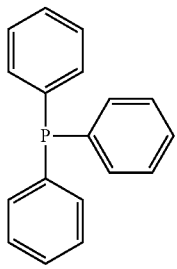 [SMILES: c1ccc(P(c2ccccc2)c2ccccc2)cc1]

Ligand g

Hydride complex H
Ir(acac-ᵗBu₂)(PPh₃)₂

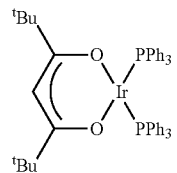

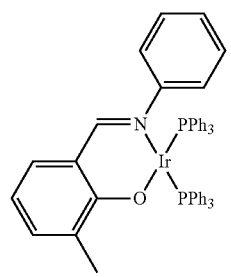

Ligand h

Hydride complex I
Ir(Ph-Im)(PPh₃)₂

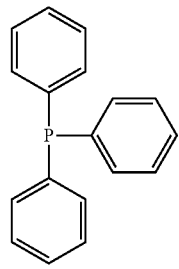

Ligand i

Reference Example 7-1

Synthesis of Iridium Complex A (Ir(acac)(P(4-MeOPh)₃)₂) (See the Synthesis Scheme Described Below)

Under argon atmosphere, tris(4-methoxyphenyl)phosphine (a) (35.2 mg, 0.10 mmol) and acetylacetonato iridium (1,5-cyclooctadiene) (20.0 mg, 0.05 mmol) were placed in a Schlenk flask. One milliliter of a degassed 1,2-dimethoxyethane was added thereto with a syringe, and the flask was tightly sealed, followed by stirring the resulting mixture at 80° C. for 3.5 hours. Thereafter, 1,2-dimethoxyethane was removed under reduced pressure, and the resultant was washed with hexane, to obtain the iridium complex A as yellow powder (44.1 mg, 0.04 mmol).

Spectroscopic Data of the Iridium Complex A:
¹H NMR (C₆D₆), δ: 7.77-7.94 (m, 12H), 6.66-6.74 (m, 12H), 5.43 (s, 1H), 3.28 (s, 18H), 1.44 (s, 6H)
³¹P[¹H] NMR (C₆D₆), δ: 13.9 (s)

[Chemical Formula 4]

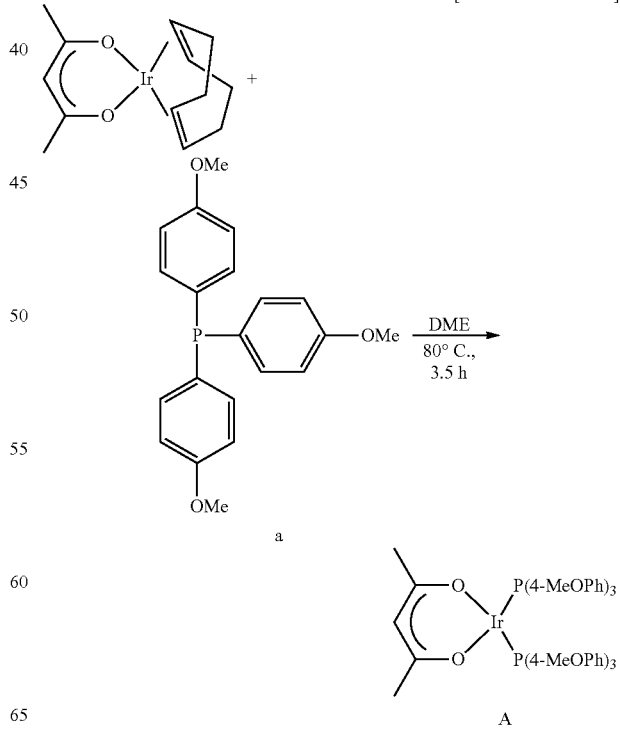

Reference Example 7-2

Synthesis of Iridium Complex B (Ir(acac)(P(4-dmaPh)Ph$_2$)$_2$)

Under argon atmosphere, acetylacetonato iridium (1,5-cyclooctadiene) (20 mg, 0.05 mmol) and (4-dimethylaminophenyl)diphenylphosphine (b) (30.5 mg, 0.10 mmol) were placed in a Schlenk flask. After addition of a degassed 1,2-dimethoxyethane (1 mL) thereto with a syringe, the flask was tightly sealed, and the mixture was stirred at room temperature for 12 hours. Thereafter, precipitated pale yellow solids were collected as the iridium complex B.
Spectroscopic Data of the Iridium Complex B:
$^1$H NMR (C$_6$D$_6$), δ: 7.94-8.03 (m, 12H), 7.00-7.20 (m, 12H), 6.37-6.39 (m, 4H), 5.40 (s, 1H), 2.43 (s, 12H), 1.38 (s, 6H)
$^{31}$P[$^1$H] NMR (C$_6$D$_6$), δ: 16.3 (s)

Reference Example 7-3

Synthesis of Iridium Complex C (Ir(acac)(PPh$_3$(MePh))$_2$)

Under argon atmosphere, acetylacetonato iridium (1,5-cyclooctadiene) (20 mg, 0.05 mmol) and diphenyl(4-methylphenyl)phosphine (c) (13.8 mg, 0.05 mmol) were placed in a Schlenk flask. After addition of a degassed 1,2-dimethoxyethane (1 mL) thereto with a syringe, the flask was tightly sealed, and the mixture was stirred at 80° C. for 12 hours. Thereafter, 1,2-dimethoxyethane was removed under reduced pressure, and washing was performed with hexane, to obtain the iridium complex C as yellow powder.

Reference Example 7-4

Synthesis of Iridium Complex D (Ir(acac)(PCy$_3$)$_2$)

Under argon atmosphere, acetylacetonato iridium (1,5-cyclooctadiene) (40 mg, 0.1 mmol) and tricyclohexylphosphine (d) (56 mg, 0.2 mmol) were placed in a Schlenk flask. After addition of a degassed 1,2-dimethoxyethane (2 mL) thereto with a syringe, the flask was tightly sealed, and the mixture was stirred at 80° C. for 3.5 hours. Thereafter, 1,2-dimethoxyethane was removed under reduced pressure, to obtain the iridium complex D as viscous brown solids.

Reference Example 7-5

Synthesis of Iridium Complex E (Ir(acac)(PBu$_3$)$_2$)

Under argon atmosphere, acetylacetonato iridium (1,5-cyclooctadiene) (26 mg, 0.05 mmol) and tributylphosphine (e) (24.6 mL, 0.10 mmol) were placed in a Schlenk flask. After addition of a degassed 1,2-dimethoxyethane (1 mL) thereto with a syringe, the flask was tightly sealed, and the mixture was stirred at room temperature for 3 hours. Thereafter, 1,2-dimethoxyethane was removed under reduced pressure, to obtain the iridium complex E as viscous brown solids.

Reference Example 7-6

Synthesis of Iridium Complex F (Ir(acac)(dppe))

Under argon atmosphere, synthetic acetylacetonato iridium bis(cyclooctene) (26 mg, 0.05 mmol) and 1,2-bis(diphenylphosphino)ethane (f) (19.9 mg, 0.05 mmol) were placed in a Schlenk flask. After addition of a degassed 1,2-dimethoxyethane (1.5 mL) thereto with a syringe, the flask was tightly sealed, and the mixture was stirred at room temperature for 24 hours. Thereafter, precipitated orange powder was collected as the iridium complex F.
Spectroscopic Data of the Iridium Complex F:
$^1$H NMR (CDCL$_3$), δ: 7.25-7.37 (m, 20H), 6.30 (s, 1H), 2.13 (s, 10H)
$^{31}$P[$^1$H] NMR (CDCL$_3$), δ: 66.5 (s)

Reference Example 7-7

Synthesis of Iridium Complex G (Ir(acac-Ph$_2$)(PPh$_3$)$_2$)

Under argon atmosphere, triphenylphosphine (g) (57.7 mg, 0.22 mmol) and synthetic (1,3-diphenyl-1,3-propanedionato)iridium (1,5-cyclooctadiene) (52.4 mg, 0.10 mmol) were placed in a Schlenk flask. After addition of 2 mL of a degassed 1,2-dimethoxyethane thereto with a syringe, the flask was tightly sealed, and the mixture was stirred at 80° C. for 3.5 hours. Thereafter, 1,2-dimethoxyethane was removed under reduced pressure, and the resultant was washed with hexane, to obtain the iridium complex G as brown powder (77.1 mg, 0.08 mmol).
Spectroscopic Data of the Iridium Complex G:
$^1$H NMR (C$_6$D$_6$), δ: 7.91-8.02 (m, 12H), 7.33-7.35 (m, 4H), 7.20-7.26 (m, 6H), 6.95-7.08 (m, 18H), 6.73 (s, 1H)
$^{31}$P[$^1$H] NMR (C$_6$D$_6$), δ: 17.9 (s)

Reference Example 7-8

Synthesis of Iridium Complex H (Ir(acac-$^t$Bu$_2$)(PPh$_3$)$_2$)

Under argon atmosphere, triphenylphosphine (h) (57.7 mg, 0.22 mmol) and synthetic (1,3-di-tert-butyl-1,3-propanedionato)iridium (1,5-cyclooctadiene) (48.4 mg, 0.10 mmol) were placed in a Schlenk flask. After addition of 2 mL of a degassed 1,2-dimethoxyethane thereto with a syringe, the flask was tightly sealed, and the mixture was stirred at 80° C. for 3.5 hours. Thereafter, 1,2-dimethoxyethane was removed under reduced pressure, and the resultant was washed with hexane, to obtain the iridium complex H as yellow powder (49.8 mg, 0.06 mmol).
Spectroscopic Data of the Iridium Complex H:
$^1$H NMR (C$_6$D$_6$), δ: 7.87-7.91 (m, 18H), 6.89-6.91 (m, 12H), 6.17 (s, 1H), 0.89 (s, 18H)
$^{31}$P[$^1$H] NMR (C$_6$D$_6$), δ: 19.1 (s)

Reference Example 7-9

Synthesis of Iridium Complex I (Ir(Ph-Im)(PPh$_3$)$_2$)

Under argon atmosphere, synthetic phenoxyimine iridium (1,5-cyclooctadiene) (51.1 mg, 0.1 mmol) and triphenylphosphine (i) (52.5 mg, 0.2 mmol) were placed in a Schlenk flask. After addition of a degassed 1,2-dimethoxyethane (2 mL) thereto with a syringe, the flask was tightly sealed, and the mixture was stirred at 80° C. for 12 hours. Thereafter, the iridium complex I was collected as precipitated orange powder.
Spectroscopic Data of the Iridium Complex I:
$^1$H NMR (C$_6$D$_6$), δ: 8.01 (s, 1H), 6.57-7.45 (m, 38H), 2.28 (s, 3H)
$^{31}$P[$^1$H] NMR (C$_6$D$_6$), δ: 6.32 (s)

Formic Acid Decomposition Reaction Using Iridium Complex: Ir(acac)L$_2$

Reference Examples 8-1 to 8-9

Figure 6:
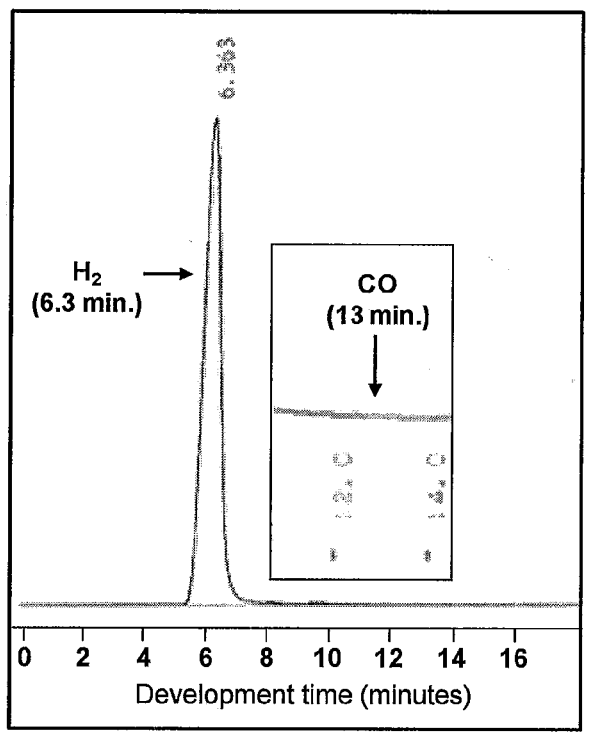
FIG. 6 shows a gas chromatogram of the generated gas and
FIG. 7 shows evaluation of durability of the iridium complex G in the formic acid decomposition reaction.

Under argon atmosphere, a predetermined amount of each of the iridium complexes (A, B, C, D, E, F, G, H and I) (5.0 μmol) and an aqueous formic acid solution (98 vol %, 0.095 mL) were placed in a glass test tube, and the test tube was sealed with a septum. The total weight of the test tube was measured, and the test tube was heated at 60° C. for 1 hour. In this reaction, the septum was punctured with a syringe needle to allow generated hydrogen and carbon dioxide to escape to the outside, to keep the pressure inside the test tube constant. After the reaction, the weight of the test tube was measured, and the catalyst turnover frequency was calculated based on the amount of decrease in the weight (catalyst turnover frequency: number of turnover per 1 hour during the initial phase of the reaction). The results for Reference Examples 8-1 to 8-9 are shown in Table 8. Qualitative analysis of the generated gas was performed using a gas chromatography apparatus (TCD), and it was confirmed that the generated gas was composed of hydrogen and carbon dioxide, and that carbon monoxide was not generated (FIG. 6).

TABLE 8

Formic Acid Decomposition Reactions Using Iridium Complexes A to I

| Reference Example | Iridium catalyst | Amount of catalyst (μmol) | Aqueous formic acid solution (mL) | Aqueous formic acid solution (vol. %) | Reaction temperature (° C.) | Reaction time (h) | Catalyst turnover frequency (h$^{-1}$) |
|---|---|---|---|---|---|---|---|
| 8-1 | A | 5.0 | 0.095 | 98 | 60 | 1 | 40 |
| 8-2 | B | 5.0 | 0.095 | 98 | 60 | 1 | 210 |
| 8-3 | C | 5.0 | 0.095 | 98 | 60 | 1 | 40 |
| 8-4 | D | 5.0 | 0.095 | 98 | 60 | 1 | 80 |
| 8-5 | E | 5.0 | 0.095 | 98 | 60 | 1 | 110 |
| 8-6 | F | 5.0 | 0.095 | 98 | 60 | 1 | 20 |
| 8-7 | G | 5.0 | 0.095 | 98 | 60 | 1 | 260 |
| 8-8 | H | 5.0 | 0.095 | 98 | 60 | 1 | 200 |
| 8-9 | I | 5.0 | 0.095 | 98 | 60 | 1 | 160 |

Reference Examples 9-1 to 9-9

Under argon atmosphere, a known iridium complex (4.8 mg, 5.0 μmol) and an aqueous formic acid solution (98 vol %, 0.095 mL) were placed in a glass test tube, and the test tube was sealed with a septum. The total weight of the test tube was measured, and the test tube was heated at 60° C. for 1 hour. In this reaction, the septum was punctured with a syringe needle to allow generated hydrogen and carbon dioxide to escape to the outside, to keep the pressure inside the test tube constant. After the reaction, the weight of the test tube was measured, and the catalyst turnover frequency was calculated based on the amount of decrease in the weight. The results for Reference Examples 9-1 to 9-9 are shown in Table 9.

TABLE 9

Formic Acid Decomposition Reactions Using Known Complexes

| Reference Example | Iridium catalyst | Amount of catalyst (μmol) | Aqueous formic acid solution (mL) | Aqueous formic acid solution (vol. %) | Reaction temperature (° C.) | Reaction time (h) | Catalyst turnover frequency (h$^{-1}$) |
|---|---|---|---|---|---|---|---|
| 9-1 | Ir(acac)(PPh$_3$)$_2$ | 5.0 | 0.095 | 98 | 60 | 1 | 250 |
| 9-2 | Ir(acac)(PPh$_2$py) | 5.0 | 0.095 | 98 | 60 | 1 | 70 |
| 9-3 | Ir(acac)(cod)$_2$ | 5.0 | 0.095 | 98 | 60 | 1 | 0 |
| 9-4 | Ru(acac)$_2$(PPh$_3$)$_2$ | 5.0 | 0.095 | 98 | 60 | 1 | 8 |
| 9-5 | Rh(acac)(PPh$_3$)$_2$ | 5.0 | 0.095 | 98 | 60 | 1 | 6 |
| 9-6 | RuCl$_2$(PPh$_3$)$_3$ | 5.0 | 0.095 | 98 | 60 | 1 | 4 |
| 9-7 | RuH$_2$(PPh$_3$)$_4$ | 5.0 | 0.095 | 98 | 60 | 1 | 40 |
| 9-8 | [RuCl$_2$(p-cymene)]$_2$ | 5.0 | 0.095 | 98 | 60 | 1 | 0 |
| 9-9 | IrH(cod)(PPh$_3$)$_2$ | 5.0 | 0.095 | 98 | 60 | 1 | 300 |

Reference Examples 10-1 to 10-7

Under argon atmosphere, the iridium complex G (2.4 mg, 2.5 mmol) and an aqueous formic acid solution (0.095 mL) at a predetermined concentration were placed in a glass test tube, and the test tube was sealed with a septum. The total weight of the test tube was measured, and the test tube was heated at 60° C. for 1 hour. In this reaction, the septum was punctured with a syringe needle to allow generated hydrogen and carbon dioxide to escape to the outside, to keep the pressure inside the test tube constant. After the reaction, the weight of the test tube was measured, and the catalyst turnover frequency was calculated based on the amount of decrease in the weight. The results for Reference Examples 10-1 to 10-7 are shown in Table 10.

TABLE 10

Influence of Formic Acid Concentration on Formic Acid Decomposition Reaction

| Reference Example | Iridium catalyst | Amount of catalyst ($\mu$mol) | Aqueous formic acid solution (mL) | Aqueous formic acid solution (vol. %) | Reaction temperature (° C.) | Reaction time (h) | Catalyst turnover frequency ($h^{-1}$) |
|---|---|---|---|---|---|---|---|
| 10-1 | G | 2.5 | 0.095 | 20 | 60 | 1 | 4 |
| 10-2 | G | 2.5 | 0.095 | 40 | 60 | 1 | 24 |
| 10-3 | G | 2.5 | 0.095 | 60 | 60 | 1 | 44 |
| 10-4 | G | 2.5 | 0.095 | 70 | 60 | 1 | 120 |
| 10-5 | G | 2.5 | 0.095 | 80 | 60 | 1 | 280 |
| 10-6 | G | 2.5 | 0.095 | 90 | 60 | 1 | 270 |
| 10-7 | G | 2.5 | 0.095 | 98 | 60 | 1 | 130 |

Reference Examples 11-1 to 11-4

Under argon atmosphere, the iridium complex G (4.8 mg, 5.0 $\mu$mol) and an aqueous formic acid solution (98 vol %, 0.095 mL) were placed in a glass test tube, and the test tube was sealed with a septum. The total weight of the test tube was measured, and the test tube was heated at a predetermined temperature for 1 hour. In this reaction, the septum was punctured with a syringe needle to allow generated hydrogen and carbon dioxide to escape to the outside, to keep the pressure inside the test tube constant. After the reaction, the weight of the Schlenk flask was measured, and the catalyst turnover frequency was calculated based on the amount of decrease in the weight. The results for Reference Examples 11-1 to 11-4 are shown in Table 11.

TABLE 11

Influence of Reaction Temperature on Formic Acid Decomposition Reaction

| Reference Example | Iridium catalyst | Amount of catalyst ($\mu$mol) | Aqueous formic acid solution (mL) | Aqueous formic acid solution (vol. %) | Reaction temperature (° C.) | Reaction time (h) | Catalyst turnover frequency ($h^{-1}$) |
|---|---|---|---|---|---|---|---|
| 11-1 | G | 5.0 | 0.095 | 98 | 55 | 60 | 110 |
| 11-2 | G | 5.0 | 0.095 | 98 | 60 | 60 | 250 |
| 11-3 | G | 5.0 | 0.095 | 98 | 70 | 40 | 570 |
| 11-4 | G | 5.0 | 0.095 | 98 | 80 | 20 | 1080 |

Reference Examples 12-1 to 12-4

Under argon atmosphere, a predetermined amount of the iridium complex G and an aqueous formic acid solution (98 vol %, 0.095 mL) were placed in a glass test tube, and the test tube was sealed with a septum. The total weight of the test tube was measured, and the test tube was heated at 60° C. for 1 hour. In this reaction, the septum was punctured with a syringe needle to allow generated hydrogen and carbon dioxide to escape to the outside, to keep the pressure inside the test tube constant. After the reaction, the weight of the test tube was measured, and the catalyst turnover frequency was calculated based on the amount of decrease in the weight. The results for Reference Examples 12-1 to 12-4 are shown in Table 12.

TABLE 12

Influence of Catalyst Concentration on Formic Acid Decomposition Reaction

| Reference Example | Iridium catalyst | Amount of catalyst (μmol) | Aqueous formic acid solution | | Reaction temperature (° C.) | Reaction time (h) | Catalyst turnover frequency ($h^{-1}$) |
|---|---|---|---|---|---|---|---|
| | | | (mL) | (vol. %) | | | |
| 12-1 | G | 1.0 | 0.095 | 98 | 60 | 1 | 40 |
| 12-2 | G | 2.5 | 0.095 | 98 | 60 | 1 | 130 |
| 12-3 | G | 5.0 | 0.095 | 98 | 60 | 1 | 250 |
| 12-4 | G | 7.0 | 0.095 | 98 | 60 | 1 | 280 |

Reference Example 13-1

Figure 7:
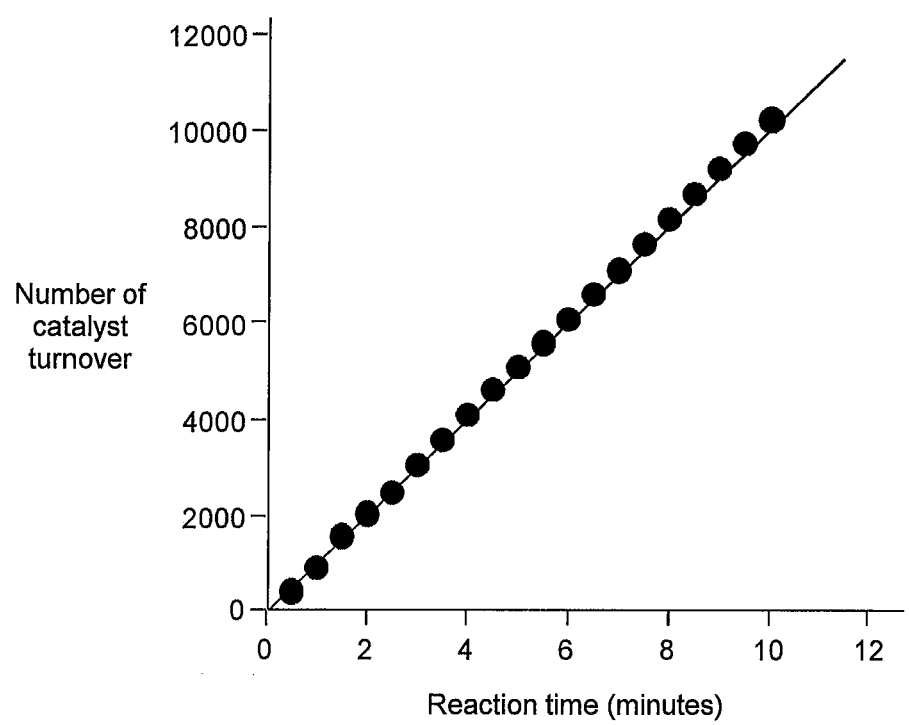

Under argon atmosphere, the iridium complex G (4.8 mg, 5.0 μmol) and an aqueous formic acid solution (98 vol %, 0.095 mL) were placed in a glass test tube, and the test tube was sealed with a septum. The total weight of the test tube was measured, and the test tube was heated at 60° C. for 1 hour. In this reaction, the septum was punctured with a syringe needle to allow generated hydrogen and carbon dioxide to escape to the outside, to keep the pressure inside the test tube constant. After the reaction, the weight of the test tube was measured, and the catalyst turnover frequency was calculated based on the amount of decrease in the weight. Thereafter, formic acid was added again to the test tube in an amount equivalent to the amount of decrease. While formic acid was added every 30 minutes in an amount equivalent to the amount of formic acid reacted, the reaction was allowed to proceed continuously for 10 hours. The result for Reference Example 13-1 is shown in FIG. 7.

Reference Example 14-1

In a screw cap test tube, the iridium hydride complex A (3 mg, 0.0025 mmol), diphenylacetylene (89 mg, 0.5 mmol), formic acid (98 vol %, 20 μL, 0.5 mmol) and, as a solvent, 1,4-dioxane (0.5 mL) were placed, and the test tube was tightly sealed under argon atmosphere. The test tube was heated using an aluminum heat block at 80° C. for 2 hours. As a result of analysis of the product with a gas chromatography apparatus, it was found that cis-stilbene was obtained in a yield of 42%, trans-stilbene was obtained in a yield of 4%, and bibenzyl was obtained in a yield of 1%. The recovery of diphenylacetylene as the raw material was 42%. That is, cis-stilbene, trans-stilbene and bibenzyl as hydrogenation products could be obtained even without addition of hydrogen gas. Since bibenzyl was produced, it was found that the iridium hydride complex A also catalyzes hydrogenation reactions of compounds having a carbon-carbon double bond (e.g., stilbene).

Example 14-2

In a screw cap test tube, the iridium hydride complex A (3 mg, 0.0025 mmol), diphenylacetylene (89 mg, 0.5 mmol), formic acid (98 vol %, 20 μL, 0.5 mmol) and, as a solvent, 1,4-dioxane (0.5 mL) were placed, and the test tube was tightly sealed under argon atmosphere. The mixture was stirred at 20° C. for 12 hours. As a result of analysis of the product with a gas chromatography apparatus, it was found that cis-stilbene was obtained in a yield of 2%, and trans-stilbene was obtained in a yield of 1%. The recovery of diphenylacetylene as the raw material was 97%. Thus, it was found that a catalytic hydrogenation reaction proceeds even under conditions at 20° C.

The invention claimed is:

1. A metal phosphine complex represented by General Formula (1):

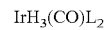

$IrH_3(CO)L_2$ wherein in Formula (1),
both Ls represent dicyclohexyl(4-dimethylaminophenyl)phosphine or 4-dimethylaminophenyldiphenylphosphine.

* * * * *